(12) United States Patent
Zablocki et al.

(10) Patent No.: US 7,022,681 B2
(45) Date of Patent: Apr. 4, 2006

(54) PARTIAL AND FULL AGONISTS OF A1 ADENOSINE RECEPTORS

(75) Inventors: Jeff Zablocki, Mountain View, CA (US); Venkata Palle, Gurgaon (IN); Elfatih Elzein, Fremont, CA (US); Xiaofen Li, Palo Alto, CA (US)

(73) Assignee: CV Therapeutics, Inc., Palo Alto, CA (US)

( * ) Notice: Subject to any disclaimer, the term of this patent is extended or adjusted under 35 U.S.C. 154(b) by 0 days.

(21) Appl. No.: 10/641,930

(22) Filed: Aug. 15, 2003

(65) Prior Publication Data

US 2004/0043960 A1    Mar. 4, 2004

Related U.S. Application Data

(60) Provisional application No. 60/403,712, filed on Aug. 15, 2002, provisional application No. 60/450,094, filed on Feb. 25, 2003.

(51) Int. Cl.
*A61K 31/70* (2006.01)
*C07H 19/167* (2006.01)

(52) U.S. Cl. ..................... 514/46; 536/27.21
(58) Field of Classification Search ............. 536/27.21; 514/46
See application file for complete search history.

(56) References Cited

U.S. PATENT DOCUMENTS

| | | | | |
|---|---|---|---|---|
| 5,140,015 A * | 8/1992 | Olsson et al. | ................. | 514/46 |
| 5,278,150 A * | 1/1994 | Olsson et al. | ................. | 514/46 |
| 5,589,467 A * | 12/1996 | Lau et al. | ...................... | 514/46 |
| RE36,494 E * | 1/2000 | Olsson et al. | ................. | 514/46 |
| 6,492,348 B1 * | 12/2002 | Bays et al. | ................... | 514/46 |
| 6,677,316 B1 * | 1/2004 | Bays et al. | ................... | 514/46 |
| 2004/0162422 A1 * | 8/2004 | Hall et al. | ................. | 536/27.3 |

FOREIGN PATENT DOCUMENTS

| EP | 0181128 B1 * | 10/1989 |
|---|---|---|
| EP | (L) 0181128 B1 * | 10/1989 |
| WO | WO 9733591 A1 | 9/1997 |
| WO | (M) WO98/16539 A1 * | 4/1998 |
| WO | WO98/16539 A1 * | 4/1998 |
| WO | WO 9967262 A1 | 12/1999 |
| WO | WO 02074780 A1 | 9/2002 |

OTHER PUBLICATIONS

Clark et al., "Partial Agonists and G Protein-Coupled Receptor Desensitization," *Trends in Pharmaceutical Science*, 20, 279-286 (Jul., 1999).*
Feoktistov et al. (I), "Adenosine $A_{2B}$ Receptors: A Novel Therapeutic Target in Asthma?" *Trends in Pharmaceutical Science*, 19, 148-153 (Apr., 1998).*
Feoktistov et al. (II), "Adenosine $A_{2B}$ Receptors as Therapeutic Targets," *Drug Development Research*, 45 (3-4), 198-206 (1998).*
Wu et al., "A Partial Agonist of the $A_1$-Adenosine Receptor Selectively Slows AV Conduction in Guinea Pig Hearts," *Am. J. Physiology* (Heart Circulation Physiology), 280(1, Pt. 2), pp. H334-H343, (Jan., 2001).*
[R] Dhalla et al., "Pharmacology and Therapeutic Applications of A1 Adenosine Receptor Ligands," □□Current Topics in Medicinal Chemistry, 3(4), 369-385 (2003).*
Dhalla et al., "Pharmacology and Therapeutic Applications of $A_1$ Adenosine Receptor Ligands," *Current Topics in Medicinal Chemistry*, 3(4), 369-385 (2003).††.*
(S) Shah et al., "Pharmacokinetics, Pharmacodynamics, and Safety of a Lipid-Lowering Adenosine A1 Agonist, RPR749, in Healthy Subjects," American Journal of Therapeutics, 11(3), 175-189 (2004).*

(Continued)

*Primary Examiner*—L. E. Crane
(74) *Attorney, Agent, or Firm*—Brian Lewis; J. Elin Hartrum; Pauline Ann Clarke

(57) ABSTRACT

Disclosed are $A_1$ adenosine receptor agonists of the formula:

Formula I wherein:
$R^1$ is optionally substituted cycloalkyl, optionally substituted heterocyclyl, optionally substituted aryl, or optionally substituted heteroaryl;
$R^2$ is hydrogen, halo, trifluoromethyl, or cyano;
$R^3$ is hydrogen, optionally substituted cycloalkyl, optionally substituted aryl, optionally substituted heteroaryl, or optionally substituted heterocyclyl,
$R^4$ and $R^5$ are independently hydrogen or optionally substituted acyl;
X is a covalent bond or lower alkylene optionally substituted by cycloalkyl;
$X^1$ is a covalent bond or alkylene;
Y is a covalent bond or lower alkylene optionally substituted by hedroxy or cycloalkyl; and
Z is —C≡C—, —$R^6$C=$CR^7$—, or —$CHR^6CHR^7$—, in which $R^6$ and $R^7$ at each occurrence are hydrogen or lower alkyl.

23 Claims, No Drawings

OTHER PUBLICATIONS (T) van Schaick et al., "Pharmacokinetic-pharmacodynamic Modelling of the Antilipolytic and Anti-Ketotic Effects of Adenosine A1-Receptor Agonist N6-(p-sulfophenyl)adenosine in Rats," British Journal of Pharmacology, 122, 525-533 (1997).*

(U) van Schaick e tal. (II), "Selectivity of Action of 8-Alkylthio Analogfues of N6-Cyclopentyladenosine in vivo: Haemodynamic versus Anti-Lipolytic Responses in Rats," British Journal of Pharmacology, 124, 607-618 (1998).*

Shah et al., "Pharmacokinitics, Pharmacodynamics, and Safety of a Lipid-Lowering Adenosine $A_1$ Agonists, RPR749, in Healthy Subjects," *American Journal of Therapeutics*, *11*(3), 175-189 (2004)††.* van Schaick et al., "Pharmacokinetic-pharmacodynamic Modelling of the Antilipolytic and Anti-Ketotic Effects of Adenosine $A_1$-Receptor Agonist N6-(p-sulfophenyl)adenosine in Rats," *British Journal of Pharmacology, 122*, 525-533 (1997).††.* van Schaick et al. (II), "Selectivity of Action of 8-Alkylthio Analogfues of $N^6$-Cyclopentyladenosine in vivo: Haemodynamic *versus* Anti-Lipolytic Responses in Rats," *British Journal of Pharmacology, 124*, 607-618 (1998).††.*

* cited by examiner

PARTIAL AND FULL AGONISTS OF A1 ADENOSINE RECEPTORS

Priority is claimed to U.S. Provisional Patent Application Ser. No. 60/403,712, filed Aug. 15, 2002, and U.S. Provisional Patent Application Ser. No. 60/450,094, filed Feb. 25, 2003, the complete disclosures of which are hereby incorporated by reference.

FIELD OF THE INVENTION

The present invention relates to novel compounds that are partial or full $A_1$ adenosine receptor agonists, and to their use in treating mammals for various disease states, including cardiovascular diseases, in particular arrhythmia and the prevention of sudden death resulting from arrhythmia, ischemia, and CNS disorders including pain, epilepsy, and emesis. $A_1$ adenosine receptor agonists are antipolytic agents, and are useful for treating metabolic disorders, including diabetes and obesity. The invention also relates to methods for their preparation, and to pharmaceutical compositions containing such compounds.

BACKGROUND

Adenosine is a naturally occurring nucleoside, which exerts its biological effects by interacting with a family of adenosine receptors known as $A_1$, $A_{2a}$, $A_{2b}$, and $A_3$, all of which modulate important physiological processes. For example, $A_{2A}$ adenosine receptors modulate coronary vasodilation, $A_{2B}$ receptors have been implicated in mast cell activation, asthma, vasodilation, regulation of cell growth, intestinal function, and modulation of neurosecretion (See Adenosine $A_{2B}$ Receptors as Therapeutic Targets, Drug Dev Res 45:198; Feoktistov et al., Trends Pharmacol Sci 19:148–153), and $A_3$ adenosine receptors modulate cell proliferation processes.

$A_1$ adenosine receptor agonists modulates the cardiostimulatory effects of catecholamine (mediated via the inhibition of adenylate cyclase), and slow the heart rate (HR) and prolong impulse propagation through the AV node, which is due in great part to activation of $I_{KAdo}$. (B. Lerman and L. Belardinelli Circulation, Vol. 83 (1991), P 1499–1509 and J. C. Shryock and L. Belardinelli The Am. J. Cardiology, Vol. 79 (1997) P 2–10). Stimulation of the $A_1$ adenosine receptor shortens the duration and decreases the amplitude of the action potential of AV nodal cells, and hence prolongs the refractory period of the AV nodal cell. Thus, stimulation of $A_1$ receptors provides a method of treating supraventricular tachycardias, including termination of nodal re-entrant tachycardias, and control of ventricular rate during atrial fibrillation and flutter.

Elevated serum levels of non-esterified free fatty acid (NEFA) are detrimental to both the mechanical and electrical function of the heart, and $A_1$ adenosine receptor agonists are potent and efficacious inhibitors of lipolysis. Importantly, because $A_1$ adenosine receptor agonists are more potent in adipose tissue that in heart tissues, they decrease lipolysis at concentrations that do not affect heart rate. Thus, $A_1$ adenosine receptor agonists are useful for treating metabolic disorders such as non-insulin-dependent diabetes mellitus and obesity via their anti-lipolytic activity. The antilipolytic effect of adenosine $A_1$ receptor agonists is also useful in the management of congestive heart failure. Furthermore, $A_1$ adenosine receptor agonists are protective against cardioischemia. $A_1$ adenosine receptor agonists are also useful as chemotherapeutics in the treatment of CNS disorders including epilepsy (anticonvulsant activity) and ischemia.

Accordingly, it is an object of this invention to provide compounds that are potent full $A_1$ adenosine receptor agonists or partial $A_1$ adenosine receptor agonists. Preferred compounds of the invention are selective for the $A_1$ adenosine receptor, which minimizes undesired side effects related to stimulation or antagonism of the other adenosine receptors.

SUMMARY OF THE INVENTION

Accordingly, in a first aspect, the invention relates to compounds of Formula I:

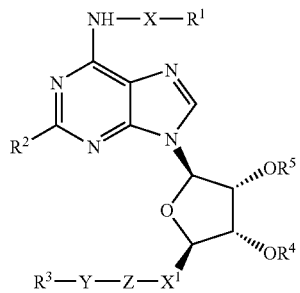

wherein:
$R^1$ is optionally substituted cycloalkyl, optionally substituted heterocyclyl, optionally substituted aryl, or optionally substituted heteroaryl;
$R^2$ is hydrogen, halo, trifluoromethyl, or cyano;
$R^3$ is hydrogen, optionally substituted cycloalkyl, optionally substituted aryl, optionally substituted heteroaryl, or optionally substituted heterocyclyl,
$R^4$ and $R^5$ are independently hydrogen or optionally substituted acyl;
X is a covalent bond or lower alkylene optionally substituted by cycloalkyl;
$X^1$ is a covalent bond or alkylene.
Y is a covalent bond or lower alkylene optionally substituted by hydroxy or cycloalkyl; and
Z is —C≡C—, —$R^6$C═$CR^7$—, or —$CHR^6CHR^7$—, in which $R^6$ and $R^7$ at each occurrence are hydrogen or lower alkyl A second aspect of the invention relates to pharmaceutical formulations, comprising a therapeutically effective amount of a compound of Formula I and at least one pharmaceutically acceptable excipient.

A third aspect of the invention relates to a method of using the compounds of Formula I in the treatment of a disease or condition in a mammal that can be effectively treated with a partial or full selective $A_1$ adenosine receptor agonist. Such diseases and conditions include at least one of the following; supraventricular tachycardia, including atrial fibrillation, and atrial flutter, ischemia, including that due to stable and unstable angina, congestive heart failure, myocardial infarction, disorders of the CNS including epilepsy and stroke, metabolic disorders, such as obesity and diabetes, or the sequela of diabetes or congestive heart failure specifically hyperlipidemia, which is alleviated by the antilipolytic effect of $A_1$ agonists on adipocytes; and the treatment of nausea (emesis).

A fourth aspect of this invention relates to methods of preparing the compounds of Formula I.

Of the compounds of Formula I, one preferred class includes those compounds in which Z is —C≡C—, particularly those compounds in which X, $X^1$ and Y are covalent bonds. A preferred group within this class includes those compounds in which $R^1$ is optionally substituted cycloalkyl optionally substituted heterocyclyl, or optionally substituted heteroaryl, and $R^2$, $R^4$ and $R^5$ are hydrogen.

A preferred subgroup includes those compounds of Formula I in which $R^3$ is hydrogen or optionally substituted aryl, especially optionally substituted phenyl. Particularly preferred compounds within this subgroup are those compounds in which $R^1$ is cycloalkyl, especially cyclopentyl or hydroxycyclopentyl, or optionally substituted heterocyclyl, especially tetrahydrofuran-3-yl, and $R^3$ is hydrogen. Other preferred compounds within this subgroup includes those compounds of Formula I in which $R^3$ is optionally substituted phenyl. Particularly preferred are those compounds in which $R^1$ is cycloalkyl, especially cyclopentyl, or optionally substituted heterocyclyl, especially tetrahydrofuran-3-yl, and $R^3$ is 2-fluorophenyl or 2-trifluoromethylphenyl.

Another preferred subgroup includes those compounds of Formula I in which $R^3$ is optionally substituted aryl. Particularly preferred compounds within this subgroup are those compounds in which $R^1$ is cycloalkyl, especially cyclopentyl, or optionally substituted heterocyclyl, especially tetrahydrofuran-3-yl. Preferred $R^3$ groups include optionally substituted thienyl, especially 5-chlorothien-2-yl.

Of the compounds of Formula I, another preferred class includes those compounds in which Z is —$R^6$C=C$R^7$—, particularly those compounds in which $R^6$ and $R^7$ are hydrogen and X, $X^1$ and Y are covalent bonds. A preferred group within this class includes those compounds in which $R^1$ is optionally substituted cycloalkyl, and $R^2$, $R^4$ and $R^5$ are hydrogen. A preferred subgroup includes those compounds of Formula I in which $R^3$ is optionally substituted aryl or optionally substituted heteroaryl. Particularly preferred are those compounds in which $R^3$ includes optionally substituted phenyl, especially phenyl or 2-methylphenyl, or optionally substituted thienyl, especially 5-chlorothien-2-yl.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain having from 1 to 20 carbon atoms. This term is exemplified by groups such as methyl, ethyl, n-propyl, iso-propyl, n-butyl, iso-butyl, t-butyl, n-hexyl, n-decyl, tetradecyl, and the like.

The term "substituted alkyl" refers to:
1) an alkyl group as defined above, having 1, 2, 3, 4 or 5 substituents, for example 1 to 3 substituents, selected from the group consisting of alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
2) an alkyl group as defined above that is interrupted by 1–10 atoms independently chosen from oxygen, sulfur and $NR_a$—, where $R_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —$S(O)_nR$, in which R is alkyl, aryl, or heteroaryl and n is 0, 1 or 2; or
3) an alkyl group as defined above that has both 1, 2, 3, 4 or 5 substituents as defined above and is also interrupted by 1–10 atoms as defined above.

The term "lower alkyl" refers to a monoradical branched or unbranched saturated hydrocarbon chain having 1, 2, 3, 4, 5, or 6 carbon atoms. This term is exemplified by groups such as methyl, ethyl, n-propyl, iso-propyl, n-butyl, iso-butyl, t-butyl, n-hexyl, and the like.

The term "substituted lower alkyl" refers to lower alkyl as defined above having 1 to 5 substituents, for example 1, 2, or 3 substituents, as defined for substituted alkyl, or a lower alkyl group as defined above that is interrupted by 1, 2, 3, 4, or 5 atoms as defined for substituted alkyl, or a lower alkyl group as defined above that has both 1, 2, 3, 4 or 5 substituents as defined above and is also interrupted by 1, 2, 3, 4, or 5 atoms as defined above.

The term "alkylene" refers to a diradical of a branched or unbranched saturated hydrocarbon chain, for example having from 1 to 20 carbon atoms, preferably 1–10 carbon atoms, more preferably 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "lower alkylene" refers to a diradical of a branched or unbranched saturated hydrocarbon chain, for example having from 1, 2, 3, 4, 5, or 6 carbon atoms.

The term "substituted alkylene" refers to:
(1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO2-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR$, where R is alkyl, aryl, or heteroaryl and n is 0, 1 or 2; or
(2) an alkylene group as defined above that is interrupted by 1–20 atoms independently chosen from oxygen, sulfur and $NR_a$—, where $R_a$ is chosen from hydrogen, optionally substituted alkyl, cycloalkyl, cycloalkenyl, aryl, heteroaryl and heterocycyl, or groups selected from carbonyl, carboxyester, carboxyamide and sulfonyl; or
(3) an alkylene group as defined above that has both 1, 2, 3, 4 or 5 substituents as defined above and is also interrupted by 1–20 atoms as defined above. Examples of substituted alkylenes are chloromethylene (—CH(Cl)—), aminoethylene (—$CH(NH_2)CH_2$—), methylaminoethylene (—CH (NHMe)CH$_2$—), 2-carboxypropylene isomers(—CH$_2$CH (CO$_2$H)CH$_2$—), ethoxyethyl (—CH$_2$CH$_2$O— CH$_2$CH$_2$—), ethylmethylaminoethyl (—CH$_2$CH$_2$N(CH$_3$) CH$_2$CH$_2$—),1-ethoxy-2-(2-ethoxy-ethoxy)ethane (—CH$_2$CH$_2$O—CH$_2$CH$_2$—OCH$_2$CH$_2$—OCH$_2$CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkoxy" refers to the group R—O—, where R is optionally substituted alkyl or optionally substituted cycloalkyl, or R is a group —Y-Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "alkylthio" refers to the group R—S—, where R is as defined for alkoxy.

The term "alkenyl" refers to a monoradical of a branched or unbranched unsaturated hydrocarbon group having from 2 to 20 carbon atoms, preferably 2 to 10 carbon atoms,and even more preferably 2 to 6 carbon atoms and having 1–6, preferably 1, double bond (vinyl). Preferred alkenyl groups include ethenyl or vinyl (—CH═CH$_2$), 1-propylene or allyl (—CH$_2$CH═CH$_2$), isopropylene (—C(CH$_3$)═CH$_2$), bicyclo[2.2.1]heptene, and the like. In the event that alkenyl is attached to nitrogen, the double bond cannot be alpha to the nitrogen.

The term "lower alkenyl" refers to alkenyl as defined above having from 2 to 6 carbon atoms.

The term "substituted alkenyl" refers to an alkenyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "alkynyl" refers to a monoradical of an unsaturated hydrocarbon having from 2 to 20 carbon atoms, preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —C≡CCH$_3$), and the like. In the event that alkynyl is attached to nitrogen, the triple bond cannot be alpha to the nitrogen.

The term "substituted alkynyl" refers to an alkynyl group as defined above having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aminocarbonyl" refers to the group —C(O)NRR where each R is independently hydrogen, alkyl, cycloaklyl, aryl, heteroaryl, heterocyclyl or where both R groups are joined to form a heterocyclic group (e.g., morpholino). Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "ester" or "carboxyester" refers to the group —C(O)OR, where R is alkyl, cycloalkyl, aryl, heteroaryl, or heterocyclyl, which may be optionally further substituted by alkyl, alkoxy, halogen, CF$_3$, amino, substituted amino, cyano, or —S(O)$_n$R$_a$, in which R$_a$ is alkyl, aryl, or heteroaryl and n is 0, 1 or 2.

The term "acylamino" refers to the group —NRC(O)R where each R is independently hydrogen, alkyl, aryl, heteroaryl, or heterocyclyl. All substituents may be optionally further substituted by alkyl, alkoxy, halogen, CF$_3$, amino, substituted amino, cyano, or —S(O)$_n$R, in which R is alkyl, aryl, or heteroaryl and n is 0, 1 or 2.

The term "acyloxy" refers to the groups —O(O)C-alkyl, —(O)C-cycloalkyl, —O(O)C-aryl, —O(O)C-heteroaryl, and —O(O)C-heterocyclyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryl" refers to an aromatic carbocyclic group of 6 to 20 carbon atoms having a single ring (e.g., phenyl) or multiple rings (e.g., biphenyl), or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with 1, 2, 3, 4 or 5 substituents, preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "aryloxy" refers to the group aryl-O— wherein the aryl group is as defined above, and includes optionally substituted aryl groups as also defined above. The term "arylthio" refers to the group R—S—, where R is as defined for aryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen, or a group —Y-Z, in which Y is optionally substituted alkylene and Z is alkenyl, cycloalkenyl, or alkynyl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "carboxyalkyl" refers to the groups —C(O)O-alkyl, —C(O)O-cycloalkyl, where alkyl and cycloalkyl, are as defined herein, and may be optionally further substituted by alkyl, alkenyl, alkynyl, alkoxy, halogen, CF$_3$, amino, substituted amino, cyano, or —S(O)$_n$R, in which R is alkyl, aryl, or heteroaryl and n is 0, 1 or 2.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and bicyclo[2.2.1]heptane, or cyclic alkyl groups to which is fused an aryl group, for example indan, and the like.

The term "substituted cycloalkyl" refers to cycloalkyl groups having 1, 2, 3, 4 or 5 substituents, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2.

The term "halogen" or "halo" refers to fluoro, bromo, chloro, and iodo.

The term "acyl" denotes a group —C(O)R, in which R is hydrogen, optionally substituted alkyl, optionally substituted cycloalkyl, optionally substituted heterocyclyl, optionally substituted aryl, and optionally substituted heteroaryl.

The term "heteroaryl" refers to an aromatic group (i.e., unsaturated) comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1, 2, or 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl (an alkyl ester), arylthio, heteroaryl, heteroarylthio, heterocyclylthio, thiol, alkylthio, aryl, aryloxy, aralkyl, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Such heteroaryl groups can have a single ring (e.g., pyridyl or furyl) or multiple condensed rings (e.g., indolizinyl, benzothiazole, or benzothienyl). Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxy-nitrogen containing heteroaryl compounds.

The term "heteroaryloxy" refers to the group heteroaryl-O—.

The term "heterocyclyl" refers to a monoradical saturated or partially unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R, where R is alkyl, aryl, or heteroaryl and n is 0, 1 or 2. Heterocyclic groups can have a single ring or multiple condensed rings. Preferred heterocyclics include tetrahydrofuranyl, morpholino, piperidinyl, and the like.

The term "thiol" refers to the group —SH.

The term "substituted alkylthio" refers to the group —S-substituted alkyl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, aryl, or heteroaryl. "Substituted sulfoxide" refers to a group —S(O)R, in which R is substituted alkyl, substituted aryl, or substituted heteroaryl, as defined herein.

The term "sulfone" refers to a group —S(O)$_2$R, in which R is alkyl, aryl, or heteroaryl. "Substituted sulfone" refers to a group —S(O)$_2$R, in which R is substituted alkyl, substituted aryl, or substituted heteroaryl, as defined herein.

The term "keto" refers to a group —C(O)—. The term "thiocarbonyl" refers to a group —C(S)—. The term "carboxy" refers to a group —C(O)—OH.

"Optional" or "optionally" means that the subsequently described event or circumstance may or may not occur, and that the description includes instances where said event or circumstance occurs and instances in which it does not.

The term "compound of Formula I" is intended to encompass the compounds of the invention as disclosed and polymorphs thereof, pharmaceutically acceptable salts, pharmaceutically acceptable esters, and prodrugs of such compounds. Additionally, the compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system. When the compound is a pure enantiomer the stereochemistry at each chiral carbon may be specified by either R or S. Resolved compounds whose absolute configuration is unknown are designated (+) or (−) depending on the direction (dextro- or laevorotary) which they rotate the plane of polarized light at the wavelength of the sodium D line.

The term "therapeutically effective amount" refers to that amount of a compound of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "treatment" or "treating" means any treatment of a disease in a mammal, including:
(i) preventing the disease, that is, causing the clinical symptoms of the disease not to develop;
(ii) inhibiting the disease, that is, arresting the development of clinical symptoms; and/or
(iii) relieving the disease, that is, causing the regression of clinical symptoms.

In many cases, the compounds of this invention are capable of forming acid and/or base salts by virtue of the presence of amino and/or carboxyl groups or groups similar thereto. The term "pharmaceutically acceptable salt" refers to salts that retain the biological effectiveness and properties of the compounds of Formula I, and which are not biologically or otherwise undesirable. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, the term "agonist" refers to the ability of a compound to interact with a receptor and evoke a maximal physiological effect (that is, activate or stimulate the receptor). This effect is known as the intrinsic efficacy. Many full agonists of the adenosine $A_1$ receptor are known to those skilled in the art, for example $N^6$-cyclopentyladenosine (CPA, or CCPA). Some adenosine $A_1$ agonists are referred to as "partial agonists" because they interact with adenosine $A_1$ receptors but produce a less than maximal response when compared to an agonist such as CPA.

The intrinsic efficacy of a compound is its differential effect on a selected tissue. Thus, a compound may be a full agonist in a given tissue but a partial in others. The compounds identified by this invention have therapeutically useful affinities for the adenosine $A_1$ receptor but have a range of intrinsic efficacies from full agonist to partial agonist. That is, some compounds may have no effect with respect to a given effector system in a given cell type, but be a full agonist in another cell type and/or effector system. A partial agonist targeted to a selected target is likely to cause fewer side effects than a full agonist, because they will be less likely to induce desensitization of the $A_1$ receptor (R. B. Clark, B. J. Knoll, R. Barber TiPS, Vol. 20 (1999) p. 279–286) and to cause side effects. Chronic administration of a full agonist (R-N6-phenylisopropyladenosine, R-PIA) for 7 days led to a desensitization of the $A_1$ receptor in terms of the dromotropic response in guinea pigs (note: a decrease in receptor number was observed—D. M. Dennis, J. C. Shryock, L. Belardinelli JPET, Vol. 272 (1995) p. 1024–1035). The $A_1$ agonist induced inhibitory effect on the production of cAMP by adenylate cyclase in adipocytes has been shown to desensitize upon chronic treatment with an $A_1$ agonist as well (W. J. Parsons and G. L. J. Biol. Chem. Vol. 262 (1987) p. 841–847).

Nomenclature

The naming and numbering of the compounds of the invention is illustrated with a representative compound of Formula I in which $R^1$ is cyclopentyl, $R^2$ is hydrogen, $R^3$ is 2-fluorophenyl, $R^4$ and $R^5$ are both hydrogen, X, $X^1$ and Y are covalent bonds, and Z is —C≡C—:

which is named: (4S,2R,3R,5R)-2-[6-(cyclopentylamino)purin-9-yl]-5-[2-(2-fluorophenyl)ethynyl]oxolane-3,4-diol, or alternatively may be named: (4S,2R,3R,5R)-2-[6-(cyclopentylamino)-9H-purin-9-yl]-5-[2-(2-fluorophenyl)ethynyl]tetrahydrofran-3,4-diol.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Synthesis of the Compounds of Formula I

The compounds of Formula I where $R^3$ is hydrogen, $X^1$ and Y are covalent bonds, and Z is —C≡C— are prepared starting from a compound of formula (1) as shown in Reaction Scheme I.

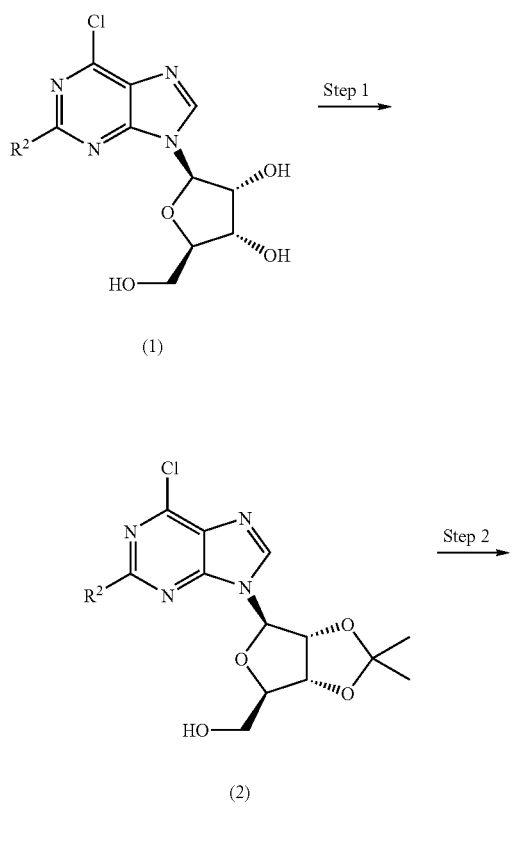

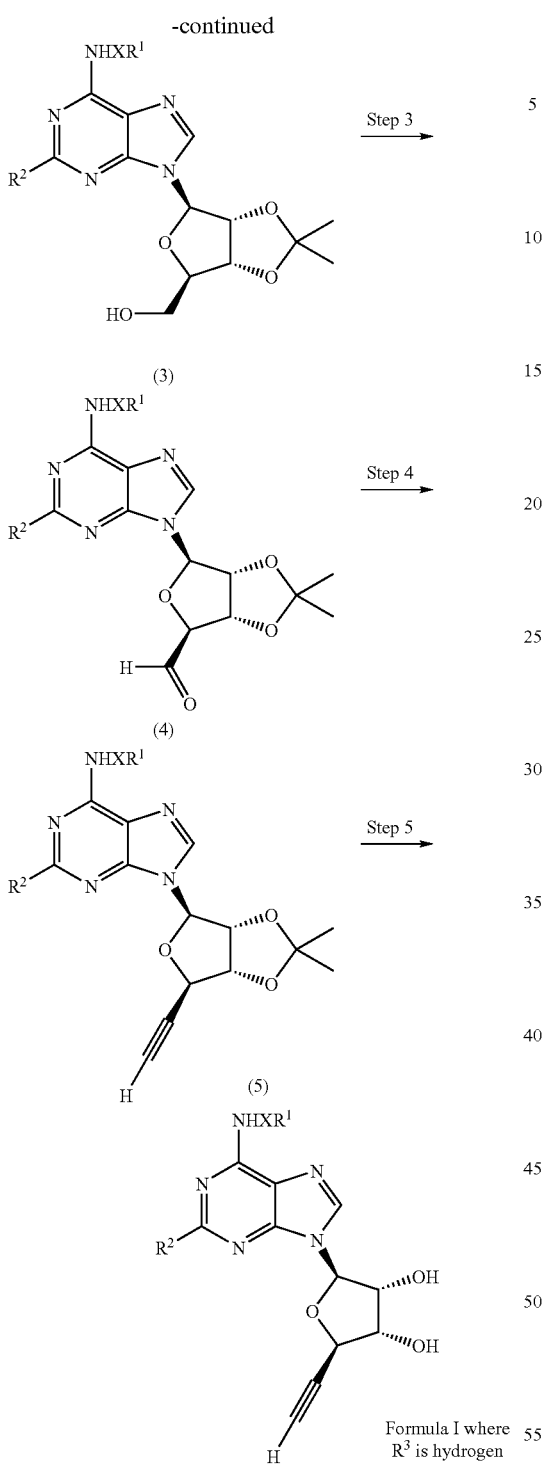

Step 1—Preparation of Formula (2)

The starting compounds of formula (1) are commercially available (for example, the compound of formula (1) in which $R^2$ is hydrogen is available from Aldrich, Milwaukee), or are prepared by means well known to those in the art. The compound of formula (2) is prepared conventionally from the compound of formula (1) by reaction with 2,2-dimethoxypropane in an inert solvent, preferably N,N-dimethylformamide, in the presence of a catalytic amount of an acid catalyst, preferably p-toluenesulfonic acid, at a temperature of about 40–90° C., preferably about 70° C., for about 24–72 hours, preferably about 48 hours. When the reaction is substantially complete, the product of formula (2) is isolated by conventional means, for example removal of the solvent under reduced pressure and purifying the residue by chromatography.

Step 2—Preparation of Formula (3)

The 6-chloro moiety is displaced from the compound of formula (2) by reaction with a compound of formula $R^1XNH_2$, where X is as defined above, in the presence of a base, for example triethylamine. The reaction is carried out in an inert protic solvent, for example ethanol, at a temperature of about reflux, for about 14–48 hours, preferably about 16 hours. When the reaction is substantially complete, the product of formula (3) is isolated by conventional means, for example by removal of the solvent under reduced pressure, followed by crystallization of the residue from a suitable solvent.

It should be noted that steps 1 and 2 may be carried out in reverse order.

Step 3—Preparation of Formula (4)

The hydroxymethyl compound of formula (3) is oxidized to an aldehyde of formula (4) using a modification of the Moffat Oxidation. In general, to the compound of formula (3) is added a mixture of 1,3-dicyclohexylcarbodiimide DCC, dimethysulfoxide and pyridine. The initial reaction is carried out at a temperature of about −5° to about 10° C., preferably about 0° C., and then at about room temperature for about 6–48 hours, preferably about 18 hours. When the reaction is substantially complete, the aldehyde of formula (4) is isolated by conventional means, for example by partitioning the product between ethyl acetate and water and removing the solvent under reduced pressure. The product is used in the next step without further purification.

Step 4—Preparation of Formula (5).

The 4'-aldehyde group is converted to an ethynyl group by reaction with bromomethyltriphenylphosphonium bromide in the presence of a strong base, preferably potassium t-butoxide. The reaction is carried out in an inert solvent, preferably tetrahydrofuran, at a temperature of about −80° C., allowing the reaction mixture to gradually warm to room temperature over a period of about 1–3 days. When the reaction is substantially complete, the product of formula (5) is isolated by conventional means, for example by removal of the solvent under reduced pressure, followed by partition between a solvent such as ethyl acetate and water, removing the solvent under reduced pressure. The residue may then be further purified by chromatography on silica gel to provide the 5'-ethynyl compound of formula (5).

Step 5—Preparation of Formula I

The acetonide-protected compound of formula (5) is then converted into a compound of Formula I in which Y is a covalent bond, Z is —C≡C—, and $R^3$ is hydrogen by treatment with an acid, for example an organic acid, for example acetic acid. The reaction is carried out in a mixture of the acid and water, at about 50–100° C., preferably about 80–90° C., for about 10–48 hours, preferably about 16 hours. When the reaction is substantially complete, the product of Formula I is isolated by conventional means, for example by removal of the solvent under reduced pressure, followed by chromatography of the residue on silica gel.

Alternative Preparation of a Compound of Formula I

The compounds of Formula I where $R^3$ is hydrogen, $X^1$ and Y are covalent bonds, and Z is —C≡C— may alternatively be prepared starting from a compound of formula (1) as shown in Reaction Scheme IA. This method of synthesis is preferred when there is substitution on the $R^1$ moiety, for example a hydroxy substituent.

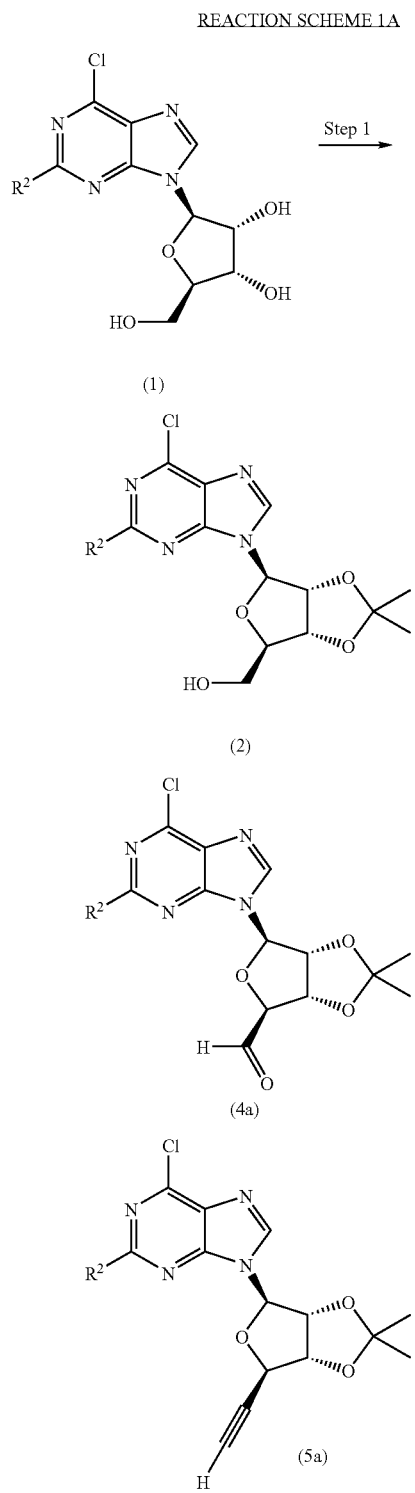

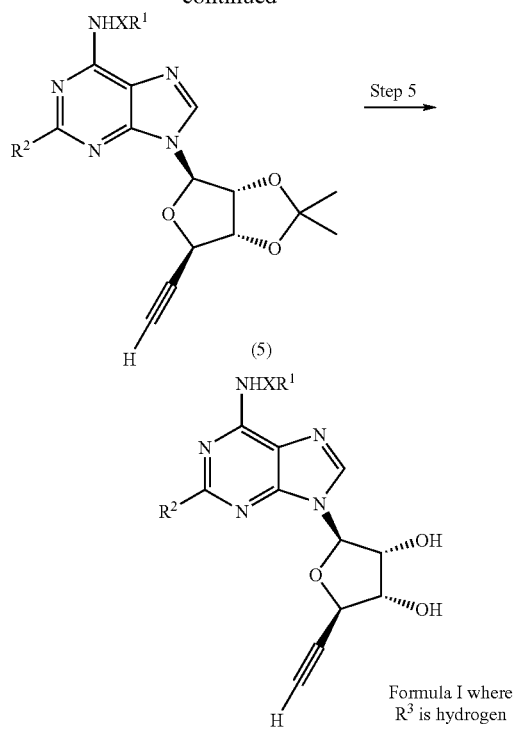

Step 1 is carried out as shown in Reaction Scheme I.

Step 2—Preparation of Formula (4a)

The hydroxymethyl compound of formula (2) is oxidized to an aldehyde of formula (4a) using a modification of the Moffat Oxidation. In general, to the compound of formula (2) is added a mixture of DCC, dimethysulfoxide and pyridine. The initial reaction is carried out at a temperature of about −5° to about 10° C., preferably about 0° C., and then at about room temperature for about 6–48 hours, preferably about 18 hours. When the reaction is substantially complete, the aldehyde of formula (4a) is isolated by conventional means, for example by partitioning the product between ethyl acetate and water and removing the solvent under reduced pressure. The product is used in the next step without further purification.

Step 3—Preparation of Formula (5a)

The 5'-aldehyde group is converted to an ethynyl group by reaction with bromomethyltriphenylphosphonium bromide in the presence of a strong base, preferably potassium t-butoxide. The reaction is carried out in an inert solvent, preferably tetrahydrofuran, at a temperature of about −80° C., allowing the reaction mixture to gradually warm to room temperature over a period of about 1–3 days. When the reaction is substantially complete, the product of formula (5a) is isolated by conventional means.

Step 4—Preparation of Formula (5)

The 6-chloro moiety is displaced from the compound of formula (5a) by reaction with a compound of formula $R^1XNH_2$, where X is as defined above, in the presence of a base, for example triethylamine. The reaction is carried out in an inert protic solvent, for example ethanol, at a temperature of about reflux, for about 14–48 hours, preferably about 16 hours. When the reaction is substantially complete, the product of Formula (5) is isolated by conventional means.

Step 5—Preparation of Formula I

The compound of formula (5) is then converted to a compound of Formula I as shown in Reaction Scheme I above.

Preparation of a Compound of Formula I in which R³ is not Hydrogen

The preparation of a compound of Formula I in which R³ is not hydrogen, X¹ is a covalent bond, Y is as defined above, and Z is —C≡C— is shown in Reaction Scheme II.

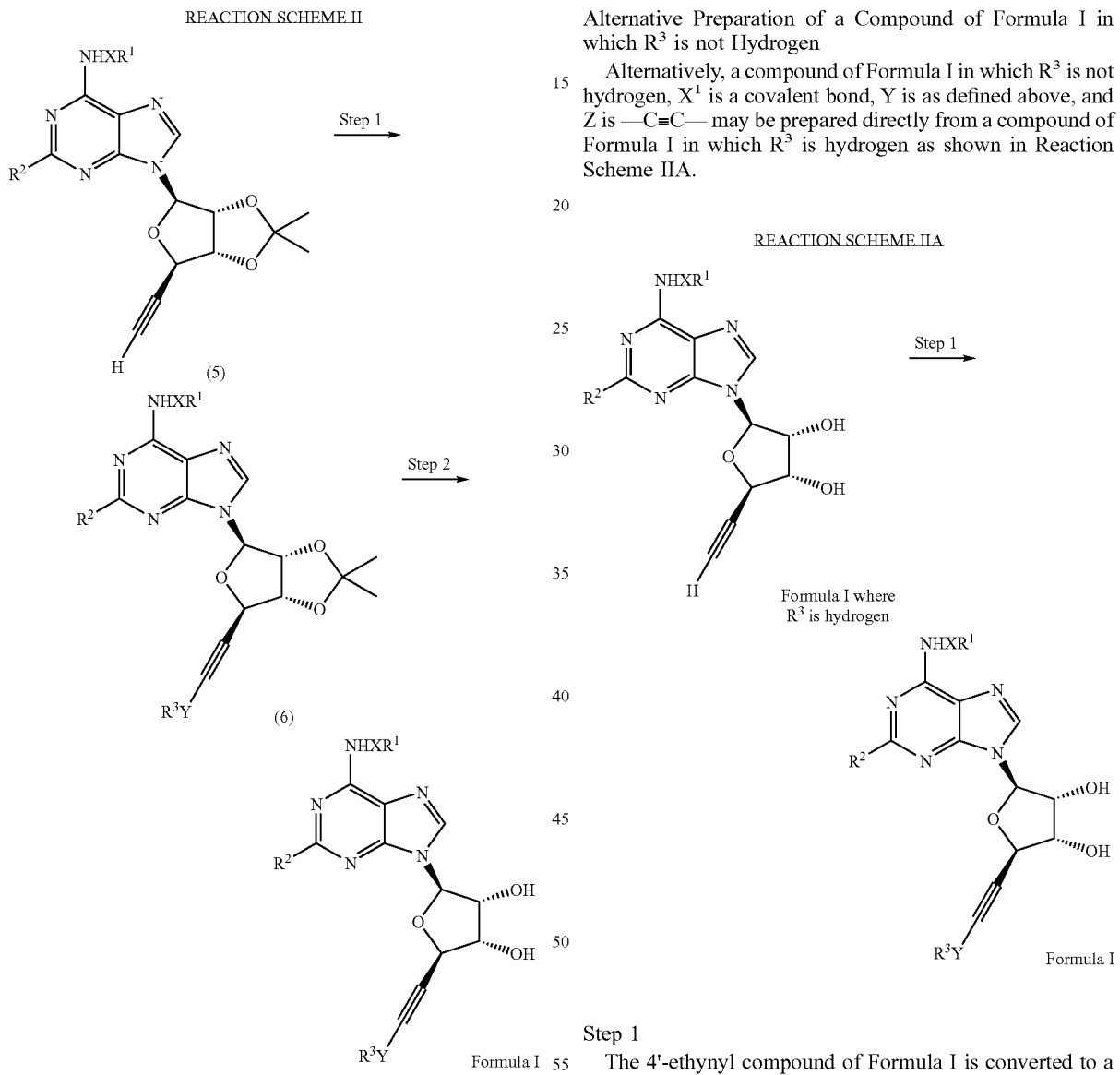

Step 1—Preparation of Formula (6)

The 4'-ethynyl compound of formula (5) is converted to a compound of formula (6) by reaction with a compound of the formula R³Y-LG, in which LG is a leaving group, preferably a halogen, for example iodo or bromo. The reaction is carried out in the presence of catalytic amounts of dichlorobis(triphenylphosphine)palladium(II) and copper(II)iodide plus a tertiary amine, for example triethylamine, in an inert solvent, for example tetrahydrofuran, at a temperature of about room temperature for about 15 minutes.

When the reaction is substantially complete, the product of Formula I is isolated by conventional means, for example by removal of the solvent under reduced pressure, followed by preparative chromatography on silica gel to provide the 5'-substituted ethynyl compound of Formula I.

Step 2—Preparation of Formula I

The compound of formula (6) is then deprotected in the same manner as shown above in Reaction Scheme 1 by treatment with an acid, preferably an organic acid, for example acetic acid, to provide a compound of Formula I.

Alternative Preparation of a Compound of Formula I in which R³ is not Hydrogen

Alternatively, a compound of Formula I in which R³ is not hydrogen, X¹ is a covalent bond, Y is as defined above, and Z is —C≡C— may be prepared directly from a compound of Formula I in which R³ is hydrogen as shown in Reaction Scheme IIA.

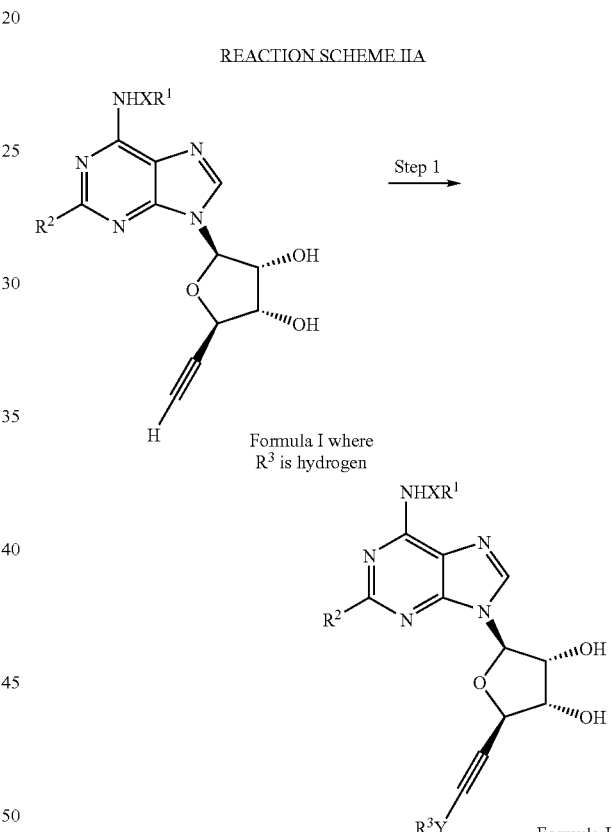

Step 1

The 4'-ethynyl compound of Formula I is converted to a compound of Formula I in which R³ is not hydrogen by reaction with a compound of the formula R³Y-LG, in which LG is a leaving group, preferably a halogen, for example iodo or bromo. The reaction is carried out in the presence of catalytic amounts of dichlorobis(triphenylphosphine)palladium(II) and copper(I)iodide plus a tertiary amine, for example triethylamine, in an inert solvent, for example tetrahydrofuran, at a temperature of about room temperature for about 15 minutes. When the reaction is substantially complete, the product of Formula I in which R³ is not hydrogen is isolated by conventional means, for example by removal of the solvent under reduced pressure, followed by preparative chromatography on silica gel to provide the 4'-substituted ethynyl compound of Formula I.

Preparation of a Compound of Formula I in which Z is —CH═CH—

The preparation of a compound of Formula I in which $X^1$ is a covalent bond and Z is —CH═CH— is shown in Reaction Scheme III.

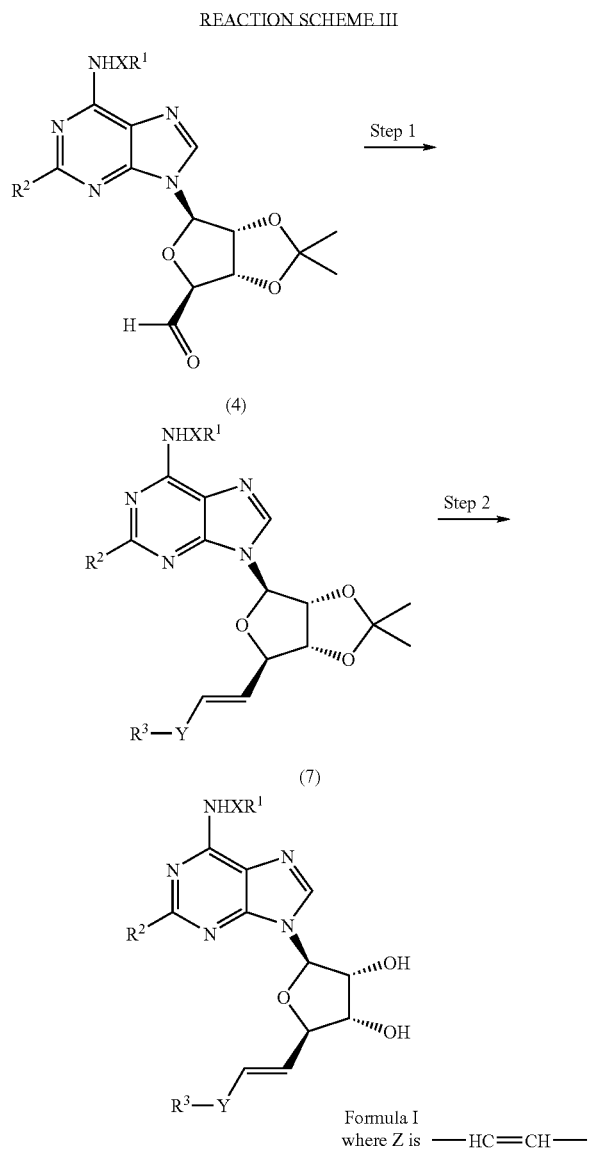

Step 1—Preparation of Formula (7)

The 4'-aldehyde group is converted to an ethenyl group using the Wittig reaction, by reaction of a compound of formula (4), the preparation of which was shown above, with $R^3Y$—$CH_2P(Ph)_3Br$ (where Ph is phenyl), in the presence of a base, for example aqueous sodium-hydroxide. The reaction is carried out in an inert solvent, for example dichloromethane, at a temperature of about room temperature, over a period of about 1–10 hours. When the reaction is substantially complete, the product of formula (7) is isolated by conventional means, for example by removal of the solvent under reduced pressure, followed by partition between a solvent such as ethyl acetate and water, removing the solvent under reduced pressure. The residue may be further purified by chromatography on silica gel to provide the 4'-ethenyl compound of formula (7).

Step 2—Preparation of a Compound of Formula I in which Z is —CH═CH—

The compound of formula (7) is then deprotected in the same manner as shown above in Reaction Scheme 1 by treatment with an acid, for example an organic acid, for example acetic acid, to provide a compound of Formula I.

Preparation of a Compound of Formula I in which Z is —$CH_2CH_2$—

The preparation of a compound of Formula I in which $X^1$ is a covalent bond and Z is —$CH_2CH_2$— is shown in Reaction Scheme IV.

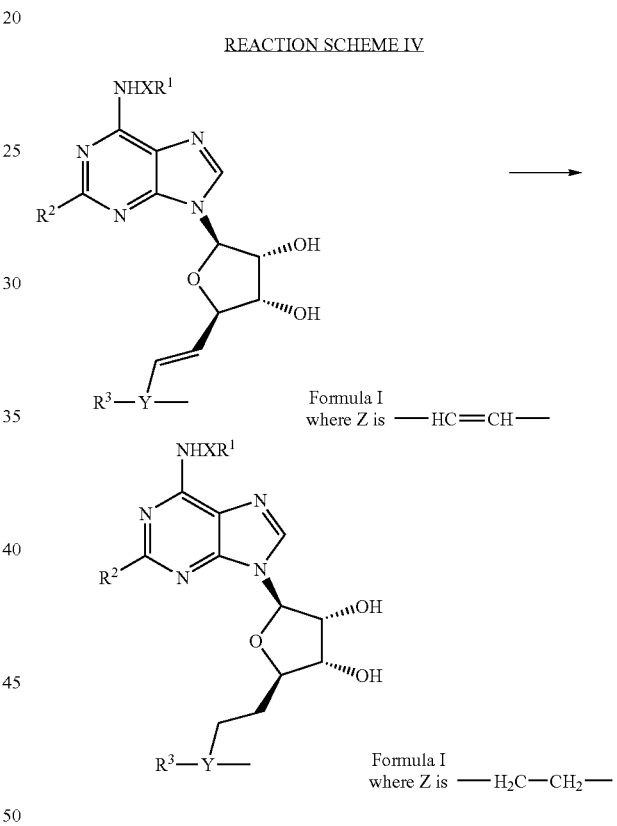

A compound of Formula I in which Z is —$CH_2CH_2$— is prepared from a compound of Formula I in which Z is —CH═CH— (or, alternatively, a compound of Formula I in which Z is —C≡C— may be used). In general, the compound of Formula I in which Z is —CH═CH— is dissolved in an inert solvent and stirred with a catalyst, for example palladium hydroxide, and a catalytic hydrogenation transfer reagent, such as cyclohexene. The reaction is carried out in an inert solvent, for example ethanol, at about room temperature, over a period of about 10–48 hours. When the reaction is substantially complete, the product of Formula I is isolated by conventional means, for example by removal of the solvent under reduced pressure, followed by chromatography, to provide a compound of Formula I in which Z is —$CH_2CH_2$—.

B. Preparation of Formula I where $R^2$ is Hydrogen and $X^1$ is $CH_2$.

The compounds of Formula I where $R^3$ is hydrogen, Y is a covalent bond, $X^1$ is $CH_2$, and Z is —C≡C— may be prepared starting from a compound of formula (4), as shown in Reaction Scheme V.

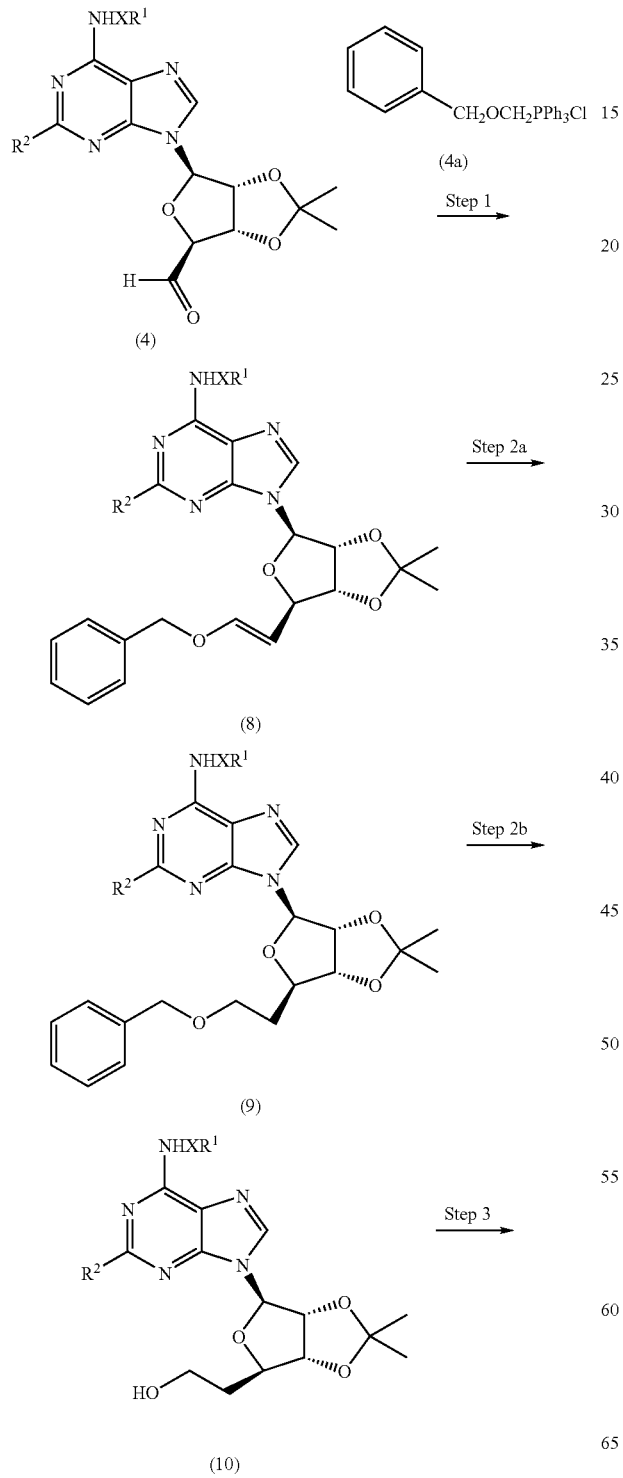

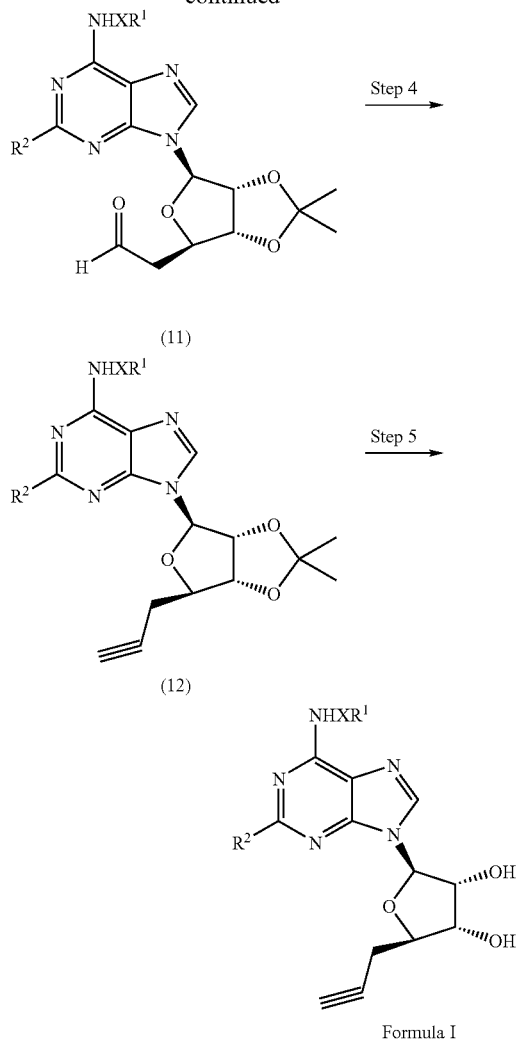

Step 1—Preparation of Formula (8)

N-sodium hexamethyldisilazane is reacted with benzyloxymethyltriphenylphosphonium chloride (formula 4a) at a temperature of about −80° C., for about 1 hour. The compound of formula (4), prepared as shown in Reaction Scheme 1, or by means well known to those in the art, is dissolved in an inert solvent, for example tetrahydrofuran, and added to the reaction mixture, which is allowed to rise to about room temperature, and stirred from 4–24 hours preferably 8 hours. When the reaction is substantially complete, the product is isolated and purified conventionally, for example by crystallization of the residue.

Step 2a. Preparation of Formula (9)

The compound of formula (9) is prepared conventionally from the compound of formula (8) by hydrogenation in the presence of with a catalyst, for example Pd/C. When the reaction is substantially complete, the product of formula (9) is isolated by conventional means and used without further purification.

Step 2b. Preparation of Formula (10)

The compound of formula (9) is deprotected by hydrogenation in the presence of a catalyst, for example palladium hydroxide, and a catalytic hydrogenation transfer reagent, such as cyclohexene. The reaction is carried out in an inert solvent, for example ethanol, at about room temperature, over a period of about 2–7 days, preferably 5 days, at about 75–100° C., preferably about 80° C. When the reaction is substantially complete, the product of formula (10) is isolated by conventional means, for example by removal of the solvent by filtration, followed by purification by chromatography on silica gel, to provide the compound of formula (10).

Step 3.—Preparation of Formula (11)

The hydroxymethyl compound of formula (10) is oxidized to an aldehyde of formula (11) using a modification of the Moffat Oxidation. In general, the compound of formula (10) is reacted with a mixture of dicyclohexylcarbodiimide, dimethylsulfoxide and pyridine. The initial reaction is carried out at a temperature of about −5°–10° C., preferably about 0° C., and then at about room temperature for about 6–48 hours, preferably about 18 hours. When the reaction is substantially complete, the aldehyde of formula (11) is isolated by conventional means. The product is for example used in the next step without further purification.

Step 4—Preparation of Formula (12)

The 4'-aldehyde group is converted to an ethynyl group by reaction with bromomethyltriphenylphosphonium bromide in the presence of a strong base, for example potassium t-butoxide. The reaction is carried out in an inert solvent, for example tetrahydrofuran, at a temperature of about −80° C., allowing the reaction mixture to gradually warm to room temperature, and stirring for about 1–3 days. When the reaction is substantially complete, the product of formula (12) is isolated and purified by conventional means, for example by chromatography on silica gel, to provide the 5'-ethynyl compound of formula (12).

Step 5—Preparation of Formula I

The acetonide-protected compound of formula (12) is then converted into a compound of Formula I in which Y is a covalent bond, Z is —C≡C—, and $R^3$ is hydrogen by treatment with an acid, for example acetic acid. The reaction is carried out in a mixture of the acid and water, at about 50–100° C., preferably about 80–90° C., for about 10–48 hours, preferably about 16 hours. When the reaction is substantially complete, the product of Formula I is isolated and purified by conventional means, for example by chromatography of the residue on silica gel.

Preparation of Compounds of Formula I where $X^1$ is $(CH_2)_2$.

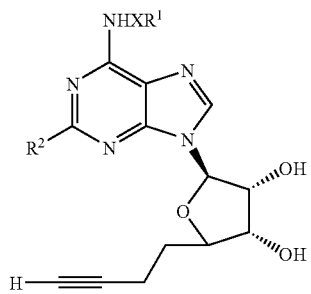

Compounds of Formula (I) where $X^1$ is $(CH_2)_2$ are obtained as shown in Reaction Scheme V but replacing the compound of Formula (4a) with a compound of Formula (4b).

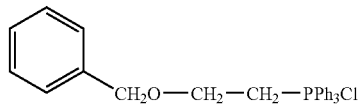

Formula (4b)

Synthesis of Compounds (4a) and (4b)

Chloro(phenylmethoxy)ethane and triphenylphosphine are reacted in an inert solvent, for example benzene, and maintained under reflux conditions overnight. When the reaction is substantially complete, the product of formula (4a) is isolated conventionally.

Similarly, by replacing chloro(phenylmethoxy) methane with chloro(phenylmethoxy) ethane, a compound of formula (4b) is prepared.

Compounds of Formula I where $X^1$ is $(CH_2)_2$ and $R^3$ is hydrogen are converted to compounds of Formula I where $X^1$ is $(CH_2)_2$ and $R^3$ is other than hydrogen as shown in Reaction Scheme II above.

Utility, Testing and Administration

General Utility

The compounds of Formula I are effective in the treatment of conditions known to respond to administration of a partial or full agonist of an $A_1$ adenosine receptor. Such conditions include, but are not limited to, acute and chronic disorders of heart rhythm, especially those diseases characterized by rapid heart rate, in which the rate is driven by abnormalities in the sinoatrial, atria, and AV nodal tissues. Such disorders include, but are not limited to, atrial fibrillation, supraventricular tachycardia and atrial flutter, congestive heart failure and sudden death resulting from arrythmia, non-insulin-dependent diabetes mellitus, hyperglycemia, epilepsy (anti-convulsant activity), and cardio- and neuro-protection.

$A_1$ agonists, as a result of their inhibitory action on cyclic AMP generation, have antilipolytic effects in adipocytes that lead to a decreased release of nonesterified fatty acids (NEFA) (E. A. van Schaick et al J. Pharmacokinetics and Biopharmaceutics, Vol. 25 (1997) p 673–694 and P. Strong Clinical Science Vol. 84 (1993) p. 663–669). Non-insulin-dependent diabetes mellitus (NIDDM) is characterized by an insulin resistance that results in hyperglycemia. Factors contributing to the observed hyperglycemia are a lack of normal glucose uptake and activation of skeletal muscle glycogen synthase (GS). Elevated levels of NEFA have been shown to inhibit insulin-stimulated glucose uptake and glycogen synthesis (D. Thiebaud et al Metab. Clin. Exp. Vol. 31 (1982) p 1128–1136 and G. Boden et al J. Clin. Invest. Vol. 93 (1994) p 2438–2446). The hypothesis of a glucose fatty acid cycle was proposed by P. J. Randle as early as 1963 (P. J. Randle et al Lancet (1963) p. 785–789). Thus, limiting the supply of fatty acids to the peripheral tissues promotes carbohydrate utilization (P. Strong et al Clinical Science Vol. 84 (1993) p. 663–669).

The benefit of an $A_1$ agonist in central nervous disorders has been reviewed (L. J. S. Knutsen and T. F. Murray In Purinergic Approaches in Experimental Therapeutics, Eds. K. A. Jacobson and M. F. Jarvis (1997) Wiley-Liss, N.Y., P—423–470). Briefly, based on experimental models of epilepsy, a mixed $A_{2A}$: $A_1$ agonist, metrifudil, has been shown to be a potent anticonvulsant against seizures induced by the inverse benzodiazepine agonist methyl 6,7- dimethoxy-4-ethyl-beta-carboline-3-carboxylate (DMCM, H. Klitgaard Eur. J. Pharmacol. (1993) Vol. 224 p. 221–228). In other studies using CGS 21680, an $A_{2A}$ agonist, it was concluded that the anticonvulsant activity was attributed to activation of the $A_1$ receptor (G. Zhang et al. Eur. J. Pharmacol. Vol. 255 (1994) p. 239–243). Furthermore, $A_1$ adenosine selective agonists have been shown to have anticonvulsant activity in the DMCM model (L. J. S. Knutsen In Adenosine and Adenne Nucleotides: From Molecular Biology to Integrative Physiology; eds. L. Belardinelli and A. Pelleg, Kluwer: Boston, 1995, pp 479–487). A second area where an $A_1$ adenosine agonist has a benefit is in animal models of forebrain ishemia as demonstrated by Knutsen et al (J. Med. Chem. Vol. 42 (1999) p. 3463–3477). The benefit in neuroprotection is believed to be in part due to the inhibition of the release of excitatory amino acids (ibid).

Testing

Activity testing is conducted as described in those patents and literature citations referenced above, and in the Examples below, and by methods apparent to one skilled in the art.

Pharmaceutical Compositions

The compounds of Formula I are usually administered in the form of pharmaceutical compositions. This invention therefore provides pharmaceutical compositions that contain, as the active ingredient, one or more of the compounds of Formula I, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The compounds of Formula I may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985) and "Modem Pharmaceutics", Marcel Dekker, Inc. $3^{rd}$ Ed. (G. S. Banker & C. T. Rhodes, Eds.).

Administration

The compounds of Formula I may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of Formula I in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of the compounds of Formula I. Administration may be via capsule or enteric coated tablets, or the like. In making the pharmaceutical compositions that include at least one compound of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds of Formula I are effective over a wide dosage range and is generally administered in a pharmaceutically effective amount. For example, for oral administration, each dosage unit contains from 10 mg to 2 g of a compound of Formula I, more preferably from 10 to 700 mg, and for parenteral administration, preferably from 10 to 700 mg of a compound of Formula I, more preferably about 50–200 mg. It will be understood, however, that the amount of the compound of Formula I actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions are administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, for example orally or nasally, from devices that deliver the formulation in an appropriate manner.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of a Compound of Formula (3)

A. Preparation of a Compound of Formula (3) where $R^1$ is Cyclopentyl, $R^2$ is Hydrogen, and X is a Covalent Bond

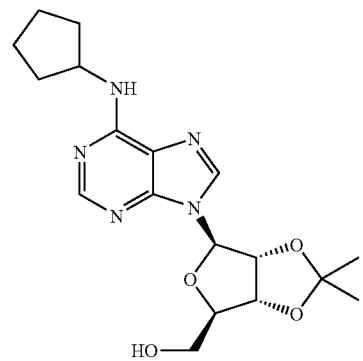

To a solution of (2S,1R,4R,5R)-2-hydroxymethyl-5-(6-chloropurin-9-yl)-tetrahydrofuran-3,4-diol acetonide, the compound of formula (2) in which $R^2$ is hydrogen (4.98 g, 15 mmol) in ethanol (80 ml) was added cyclopentylamine (0.6 ml, 30 mmol) and triethylamine (6.27 ml, 45 mmol), and the mixture was refluxed for 16 hours. The solvent was then removed under reduced pressure, and the residue partitioned between ethyl acetate and 10% citric acid in water, followed by water. Ethyl acetate was removed from the organic layer, to yield {(1R,2R,4R,5R)-4-[6-(cyclopentylamino)purin-9-yl]-7,7-dimethyl-3,6,8-trioxabicyclo[3.3.0]oct-2-yl}methan-1-ol, a compound of formula (3).

B. Preparation of Compounds of Formula (3), Varying X, $R^1$ and $R^2$

Similarly, following the procedure of 1A above, but replacing cyclopentylamine with other amines of formula $R^1XNH_2$, the following compound of formula (3) was prepared:
{(1R,2R,4R,5R)-7,7-dimethyl-3,6,8-trioxa-4-[6-(oxolan-3-ylamino)purin-9-yl]bicyclo[3.3.0]oct-2-yl}methan-1-ol.

C. Preparation of Compounds of Formula (3), Varying X, $R^1$ and $R^2$

Similarly, following the procedure of 1A above, but replacing cyclopentylamine with other amines of formula $R^1XNH_2$, the following compounds of formula (3) are prepared:
{(1R,2R,4R,5R)-4-[6-(cyclopentylmethylamino)purin-9-yl]-7,7-dimethyl-3,6,8-trioxabicyclo[3.3.0]oct-2-yl}methan-1-ol;
{(1R,2R,4R,5R)-4-[2-trifluoromethyl-6-(cyclopentylamino)purin-9-yl]-7,7-dimethyl-3,6,8-trioxabicyclo[3.3.0]oct-2-yl}methan-1-ol;
{(1R,2R,4R,5R)-4-[6-cyclobutylamino)purin-9-yl]-7,7-dimethyl-3,6,8-trioxabicyclo[3.3.0]oct-2-yl}methan-1-ol;
{(1R,2R,4R,5R)-4-[6-cyclohexylamino)purin-9-yl]-7,7-dimethyl-3,6,8-trioxabicyclo[3.3.0]oct-2-yl}methan-1-ol;
{(1R,2R,4R,5R)-4-[2-fluoro-6-cyclohexylamino)purin-9-yl]-7,7-dimethyl-3,6,8-trioxabicyclo[3.3.0]oct-2-yl}methan-1-ol;

{(1R,2R,4R,5R)-4-[6-cyclohexylmethylamino)purin-9-yl]-7,7-dimethyl-3,6,8-trioxabicyclo[3.3.0]oct-2-yl}methan-1-ol;
{(1R,2R,4R,5R)-4-[6-(3-fluorocyclopentylamino)purin-9-yl]-7,7-dimethyl-3,6,8-trioxabicyclo[3.3.0]oct-2-yl}methan-1-ol;
{(1R,2R,4R,5R)-4-[6-(4-trifluoromethylcyclopentylamino)purin-9-yl]-7,7-dimethyl-3,6,8-trioxabicyclo[3.3.0]oct-2-yl}methan-1-ol;
{(1R,2R,4R,5R)-4-[6-(3-methoxycyclopentylamino)purin-9-yl]-7,7-dimethyl-3,6,8-trioxabicyclo[3.3.0]oct-2-yl}methan-1-ol;
{(1R,2R,4R,5R)-4-[6-(phenylamino)purin-9-yl]-7,7-dimethyl-3,6,8-trioxabicyclo[3.3.0]oct-2-yl}methan-1-ol;
{(1R,2R,4R,5R)-4-[6-(benzylamino)purin-9-yl]-7,7-dimethyl-3,6,8-trioxabicyclo[3.3.0]oct-2-yl}methan-1-ol;
{(1R,2R,4R,5R)-4-[6-(4-fluorophenylamino)purin-9-yl]-7,7-dimethyl-3,6,8-trioxabicyclo[3.3.0]oct-2-yl}methan-1-ol;
{(1R,2R,4R,5R)-4-[6-(pyridin-3-ylamino)purin-9-yl]-7,7-dimethyl-3,6,8-trioxabicyclo[3.3.0]oct-2-yl}methan-1-ol;
{(1R,2R,4R,5R)-4-[6-(thiazol-2-ylamino)purin-9-yl]-7,7-dimethyl-3,6,8-trioxabicyclo[3.3.0]oct-2-yl}methan-1-ol;
{(1R,2R,4R,5R)-4-[6-(tetrahydropyran-3-ylamino)purin-9-yl]-7,7-dimethyl-3,6,8-trioxabicyclo[3.3.0]oct-2-yl}methan-1-ol;
{(1R,2R,4R,5R)-4-[6-(tetrahydropyran-3-ylmethylamino)purin-9-yl]-7,7-dimethyl-3,6,8-trioxabicyclo[3.3.0]oct-2-yl}methan-1-ol; and
{(1R,2R,4R,5R)-4-[6-(5-fluorotetrahydropyran-3-ylamino)purin-9-yl]-7,7-dimethyl-3,6,8-trioxabicyclo[3.3.0]oct-2-yl}methan-1-ol.

D. Preparation of Compounds of Formula (3), Varying X, $R^1$ and $R^2$

Similarly, following the procedure of 1A above, but replacing cyclopentylamine with other amines of formula $R^1XNH_2$, other compounds of formula (3) are prepared.

EXAMPLE 2

Preparation of a Compound of Formula (4)

A. Preparation of a Compound of Formula (4) where $R^1$ is Cyclopentyl $R^2$ is Hydrogen and X is a Covalent Bond

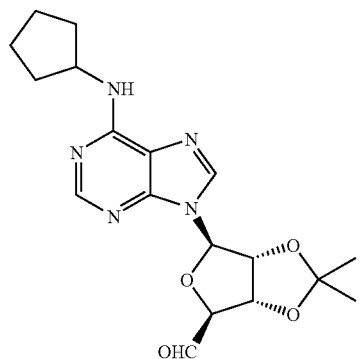

A mixture of {(1R,2R,4R,5R)-4-[6-(cyclopentylamino)purin-9-yl]-7,7-dimethyl-3,6,8-trioxabicyclo[3.3.0]oct-2-yl}methan-1-ol (0.94 g, 25 mmol), dimethylsulfoxide (7 ml), dicyclohexylcarbodimide (1.55 g) and pyridine (0.2 ml) was stirred at 0° C. for a few minutes, and then trifluoro-acetic acid (0.1 ml) added. The mixture was allowed to warm to room temperature, and stirred for 18 hours. The mixture was then partitioned between ethyl acetate and water and washed with water. Solvent was removed from the organic layer under reduced pressure, and the product, (2S,1R,4R,5R)-4-[6-(cyclopentylamino)purin-9-yl]-7,7-dimethyl-3,6,8-trioxabicyclo[3.3.0]octane-2-carbaldehyde, a compound of formula (4).

B. Preparation of Compounds of Formula (4), Varying $R^1$

Similarly, following the procedure of 2A above, but replacing {(1R,2R,4R,5R)-4-[6-(cyclopentylamino)purin-9-yl]-7,7-dimethyl-3,6,8-trioxabicyclo[3.3.0]oct-2-yl}methan-1-ol with {(1R,2R,4R,5R)-7,7-dimethyl-3,$^6$,$^8$-trioxa-4-[6-(oxolan-3-ylamino)purin-9-yl]bicyclo[3.3.0]oct-2-yl}methan-1-ol, the following compound of formula (4) was prepared:
(2S,1R,4R,5R)-7,7-dimethyl-3,6,8-trioxa-4-[6-(oxolan-3-ylamino)purin-9-yl]bicyclo[3.3.0]octane-2-carboxaldehyde.

C. Preparation of Compounds of Formula (4), Varying X, $R^1$ and $R^2$

Similarly, following the procedure of 2A above, but replacing {(1R,2R,4R,5R)-4-[6-(cyclopentylamino)purin-9-yl]-7,7-dimethyl-3,6,8-trioxabicyclo[3.3.0]oct-2-yl}methan-1-ol with other compounds of formula (3), the following compounds of formula (4) are prepared:
{(1R,2R,4R,5R)-4-[6-(cyclopentylmethylamino)purin-9-yl]-7,7-dimethyl-3,6,8-trioxabicyclo[3.3.0]octane-2-carboxaldehyde;
{(1R,2R,4R,5R)-4-[2-trifluoromethyl-6-(cyclopentylamino)purin-9-yl]-7,7-dimethyl-3,6,8-trioxabicyclo[3.3.0]octane-2-carboxaldehyde;
{(1R,2R,4R,5R)-4-[6-cyclobutylamino)purin-9-yl]-7,7-dimethyl-3,6,8-trioxabicyclo[3.3.0]octane-2-carboxaldehyde;
{(1R,2R,4R,5R)-4-[6-cyclohexylamino)purin-9-yl]-7,7-dimethyl-3,6,8-trioxabicyclo[3.3.0]octane-2-carboxaldehyde;
{(1R,2R,4R,5R)-4-[2-fluoro-6-cyclohexylamino)purin-9-yl]-7,7-dimethyl-3,6,8-trioxabicyclo[3.3.0]octane-2-carboxaldehyde;
{(1R,2R,4R,5R)-4-[6-cyclohexylmethylamino)purin-9-yl]-7,7-dimethyl-3,6,8-trioxabicyclo[3.3.0]octane-2-carboxaldehyde;
{(1R,2R,4R,5R)-4-[6-(3-fluorocyclopentylamino)purin-9-yl]-7,7-dimethyl-3,6,8-trioxabicyclo[3.3.0]octane-2-carboxaldehyde;
{(1R,2R,4R,5R)-4-[6-(4-trifluoromethylcyclopentylamino)purin-9-yl]-7,7-dimethyl-3,6,8-trioxabicyclo[3.3.0]octane-2-carboxaldehyde;
{(1R,2R,4R,5R)-4-[6-(3-methoxycyclopentylamino)purin-9-yl]-7,7-dimethyl-3,6,8-trioxabicyclo[3.3.0]octane-2-carboxaldehyde;
{(1R,2R,4R,5R)-4-[6-(phenylamino)purin-9-yl]-7,7-dimethyl-3,6,8-trioxabicyclo[3.3.0]octane-2-carboxaldehyde;
{(1R,2R,4R,5R)-4-[6-(benzylamino)purin-9-yl]-7,7-dimethyl-3,6,8-trioxabicyclo[3.3.0]octane-2-carboxaldehyde;
{(1R,2R,4R,5R)-4-[6-(4-fluorophenylamino)purin-9-yl]-7,7-dimethyl-3,6,8-trioxabicyclo[3.3.0]octane-2-carboxaldehyde;
{(1R,2R,4R,5R)-4-[6-(pyridin-3-ylamino)purin-9-yl]-7,7-dimethyl-3,6,8-trioxabicyclo[3.3.0]octane-2-carboxaldehyde;
{(1R,2R,4R,5R)-4-[6-(thiazol-2-ylamino)purin-9-yl]-7,7-dimethyl-3,6,8-trioxabicyclo[3.3.0]octane-2-carboxaldehyde;

{(1R,2R,4R,5R)-4-[6-(tetrahydropyran-3-ylamino)purin-9-yl]-7,7-dimethyl-3,6,8-trioxabicyclo[3.3.0]octane-2-carboxaldehyde;

{(1R,2R,4R,5R)-4-[6-(tetrahydropyran-3-ylmethylamino)purin-9-yl]-7,7-dimethyl-3,6,8-trioxabicyclo[3.3.0]octane-2-carboxaldehyde; and {(1R,2R,4R,5R)-4-[6-(5-fluorotetrahydropyran-3-ylamino)purin-9-yl]-7,7-dimethyl-3,6,8-trioxabicyclo[3.3.0]octane-2-carboxaldehyde.

D. Preparation of Compounds of Formula (4), Varying X, $R^1$ and $R^2$

Similarly, following the procedure of 2A above, but replacing {(1R,2R,4R,5R)-4-[6-(cyclopentylamino)purin-9-yl]-7,7-dimethyl-3,6,8-trioxabicyclo[3.3.0]oct-2-yl}methan-1-ol with other compounds of formula (3), other compounds of formula (4) are prepared.

EXAMPLE 3

Preparation of a Compound of Formula (5)

A. Preparation of a Compound of Formula (5) where $R^1$ is Cyclopentyl and $R^2$ is Hydrogen

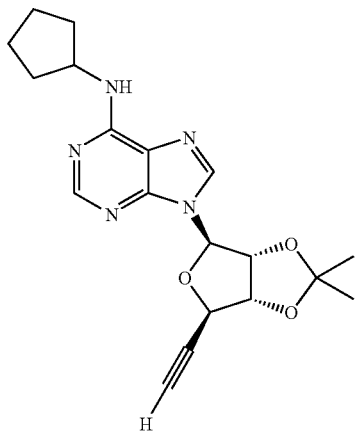

To a suspension of potassium t-butoxide (0.84 g, 7.5 mmol) in tetrahydrofuran (5 ml) at −78° C. was added bromomethyltriphenylphosphonium (1.64 g, 3.75 mmol) in small portions, and the mixture stirred for 2 hours. To this mixture was added a solution of (2S,1R,4R,5R)-4-[6-(cyclopentylamino)purin-9-yl]-7,7-dimethyl-3,6,8-trioxabicyclo[3.3.0]octane-2-carboxaldehyde (0.932 g, 2.5 mmol) in tetrahydrofuran (20 ml), and the mixture was stirred for 2 hours at −78° C. The reaction mixture was then allowed to warm to room temperature and stirred for 6 days, then quenched with aqueous ammonium chloride, and partitioned between water and ethyl acetate. The organic layer was separated, dried over magnesium sulfate, filtered, and the solvent removed from the filtrate under reduced pressure, to yield [9-((1R,2S,4R,5R)-4-ethynyl-7,7-dimethyl-3,6,8-trioxabicyclo[3.3.0]oct-2-yl)purin-9-yl]cyclopentylamine, a compound of formula (5).

B. Preparation of Compounds of Formula (5), Varying $R^1$

Similarly, following the procedure of 3A above, but replacing (2S,1R,4R,5R)-4-[6-(cyclopentylamino)purin-9-yl]-7,7-dimethyl-3,6,8-trioxabicyclo[3.3.0]octane-2-carboxaldehyde with {(1R,2S,4R,5R)-7,7-dimethyl-3,6,8-trioxa-4-[6-(oxolan-3-ylamino)purin-9-yl]bicyclo[3.3.0]octane-2-carboxaldehyde, the following compound of formula (5) was prepared:

(1R,2R,4R,5R)-4-ethynyl-7,7-dimethyl-3,6,8-trioxa bicyclo[3.3.0]oct-2-yl)-purin-9-ylamine.

C. Preparation of Compounds of Formula (4) Varying X, $R^1$ and $R^2$

Similarly, following the procedure of 3A above, but replacing {(1R,2R,4R,5R)-4-[6-(cyclopentylamino)purin-9-yl]-7,7-dimethyl-3,6,8-trioxabicyclo[3.3.0]oct-2-yl}methan-1-ol with other compounds of formula (3), the following compounds of formula (4) are prepared:

{(1R,2R,4R,5R)-4-ethynyl-7,7-dimethyl-3,6,8-trioxabicyclo[3.3.0]oct-2-yl-purin-9-yl]cyclopentylmethylamine;

{(1R,2R,4R,5R)-4-ethynyl-7,7-dimethyl-2-trifluoromethyl-3,6,8-trioxabicyclo[3.3.0]oct-2-yl-purin-9-yl]cyclopentylamine;

{(1R,2R,4R,5R)-4-ethynyl-7,7-dimethyl-3,6,8-trioxabicyclo[3.3.0]oct-2-yl-purin-9-yl]cyclobutylamine;

{(1R,2R,4R,5R)-4-ethynyl-7,7-dimethyl-3,6,8-trioxabicyclo[3.3.0]oct-2-yl-purin-9-yl]cyclohexylamine;

{(1R,2R,4R,5R)-4-ethynyl-7,7-dimethyl-3,6,8-trioxabicyclo[3.3.0]oct-2-yl-purin-9-yl]2-flouro-6-cyclohexylamine;

{(1R,2R,4R,5R)-4-ethynyl-7,7-dimethyl-3,6,8-trioxabicyclo[3.3.0]oct-2-yl-purin-9-yl]cyclohexylmethylamine;

{(1R,2R,4R,5R)-4-ethynyl-7,7-dimethyl-3,6,8-trioxabicyclo[3.3.0]oct-2-yl-purin-9-yl](3-fluorocyclopentylamine;

{(1R,2R,4R,5R)-4-ethynyl-7,7-dimethyl-3,6,8-trioxabicyclo[3.3.0]oct-2-yl-purin-9-yl](4-trifluoromethylcyclopentylamine;

{(1R,2R,4R,5R)-4-ethynyl-7,7-dimethyl-3,6,8-trioxabicyclo[3.3.0]oct-2-yl-purin-9-yl](3-methoxycyclopentylamine;

{(1R,2R,4R,5R)-4-ethynyl-7,7-dimethyl-3,6,8-trioxabicyclo[3.3.0]oct-2-yl-purin-9-yl](phenylamine;

{(1R,2R,4R,5R)-4-ethynyl-7,7-dimethyl-3,6,8-trioxabicyclo[3.3.0]oct-2-y-purin-9-yl]benzylamine;

{(1R,2R,4R,5R)-4-ethynyl-7,7-dimethyl-3,6,8-trioxabicyclo[3.3.0]oct-2-yl-purin-9-yl](4-fluorophenylamine);

{(1R,2R,4R,5R)-4-ethynyl-7,7-dimethyl-3,6,8-trioxabicyclo[3.3.0]oct-2-yl-purin-9-yl](pyridin-3-ylamine;

{(1R,2R,4R,5R)-4-ethynyl-7,7-dimethyl-3,6,8-trioxabicyclo[3.3.0]oct-2-ylpurin-9-yl](thiazol-2-ylamine;

{(1R,2R,4R,5R)-4-ethynyl-7,7-dimethyl-3,6,8-trioxabicyclo[3.3.0]oct-2-yl-purin-9-yl](tetrahydropyran-3-ylamine);

{(1R,2R,4R,5R)-4-ethynyl-7,7-dimethyl-3,6,8-trioxabicyclo[3.3.0]oct-2-yl-purin-9-yl](tetrahydropyran-3-ylmethylamine; and {(1R,2R,4R,5R)-4-ethynyl-7,7-dimethyl-3,6,8-trioxabicyclo[3.3.0]oct-2-yl-purin-9-yl](5-fluorotetrahydropyran-3-ylamine.

D. Preparation of Compounds of Formula (5), Varying X, $R^1$ and $R^2$

Similarly, following the procedure of 3A above, but replacing {(1R,2R,4R,5R)-4-[6-(cyclopentylamino)purin-9-yl]-7,7-dimethyl-3,6,8-trioxabicyclo[3.3.0]oct-2-yl}methan-1-ol with other compounds of formula (4), other compounds of formula (5) are prepared.

EXAMPLE 4

Preparation of a Compound of Formula I

A. Preparation of a Compound of Formula I where $R^1$ is Cyclopentyl, $R^2$, $R^3$, $R^4$ and $R^5$ are Hydrogen, X, $X^1$ and Y are Covalent Bonds, and Z is —C≡C—

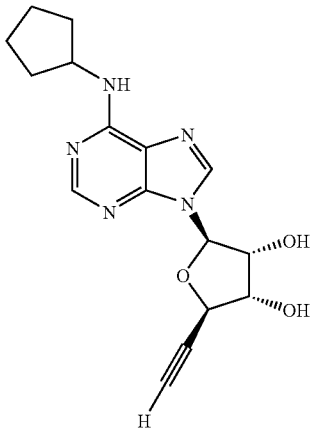

A solution of [9-((1R,2R,4R,5R)-4-ethynyl-7,7-dimethyl-3,6,8-trioxabicyclo[3.3.0]oct-2-yl)purin-6-yl]cyclopentylamine (0.28 g) was dissolved in 20 ml of a mixture of acetic acid:water (80:20) and stirred overnight at 75° C. Solvent was removed under reduced pressure, and the residue purified by preparative TLC, eluting with methanol:methylene chloride (1:8), to yield (4S,2R,3R,5R)-2-[6-(cyclopentylamino)purin-9-yl]-5-ethynyloxolane-3,4-diol, a compound of Formula I.

B. Preparation of a Compound of Formula I where $R^1$ is Tetrahydrofuran-3-yl, $R^2$, $R^3$, $R^4$ and $R^5$ are Hydrogen, X, $X^1$ and Y are Covalent Bonds, and Z is —C≡C—

Similarly, following the procedure of 4A above, but replacing [9-((1R,2R,4R,5R)-4-ethynyl-7,7-dimethyl-3,6,8-trioxabicyclo[3.3.0]oct-2-yl)purin-6-yl]cyclopentylamine with (1R,2R,4R,5R)-4-ethynyl-7,7-dimethyl-3,6,8-trioxabicyclo[3.3.0]oct-2-yl)-purin-9-yl]oxolan-3-ylamine, the following compounds of Formula I are prepared:

(4S,2R,3R,5R)-2-[6-(oxolan-3-ylamino)purin-9-yl]-5-ethynyloxolane-3,4-diol;
(4S,2R,3R,5R)-2-[6-(cyclopentylmethylamino)purin-9-yl]-5-ethynyloxolane-3,4-diol;
(4R,2R,3R,5R)-2-[2-trifluoromethyl-6-(cyclopentylamino)purin-9-yl]-5-ethynyloxolane-3,4-diol;
(4S,2R,3R,5R)-2-[6-(cyclobutylamino)purin-9-yl]-5-ethynyloxolane-3,4-diol;
(4S,2R,3R,5R)-2-[6-(cyclohexylamino)purin-9-yl]-5-ethynyloxolane-3,4-diol;
(4S,2R,3R,5R)-2-[2-fluoro-6-(cyclohexylamino)purin-9-yl]-5-ethynyloxolane-3,4-diol;
(4S,2R,3R,5R)-2-[6-(cyclohexylmethylamino)purin-9-yl]-5-ethynyloxolane-3,4-diol;
(4S,2R,3R,5R)-2-[6-(3-fluorocyclopentylamino)purin-9-yl]-5-ethynyloxolane-3,4-diol;
(4S,2R,3R,5R)-2-[6-(4-trifluoromethylcyclopentylamino)purin-9-yl]-5-ethynyloxolane-3,4-diol;
(4S,2R,3R,5R)-2-[6-(3-methoxycyclopentylamino)purin-9-yl]-5-ethynyloxolane-3,4-diol;
(4S,2R,3R,5R)-2-[6-(phenylamino)purin-9-yl]-5-ethynyloxolane-3,4-diol;
(4S,2R,3R,5R)-2-[6-(benzylamino)purin-9-yl]-5-ethynyloxolane-3,4-diol;
(4S,2R,3R,5R)-2-[6-(4-fluorophenylamino)purin-9-yl]-5-ethynyloxolane-3,4-diol;
(4S,2R,3R,5R)-2-[6-(pyridin-3-ylamino)purin-9-yl]-5-ethynyloxolane-3,4-diol;
(4S,2R,3R,5R)-2-[6-(thiazol-2-ylamino)purin-9-yl]-5-ethynyloxolane-3,4-diol;
(4S,2R,3R,5R)-2-[6-(tetrahydropyran-3-ylamino)purin-9-yl]-5-ethynyloxolane-3,4-diol;
(4S,2R,3R,5R)-2-[6-(tetrahydropyran-3-ylmethylamino)purin-9-yl]-5-ethynyloxolane-3,4-diol; and
(4S,2R,3R,5R)-2-[6-(5-fluorotetrahydropyran-3-ylamino)purin-9-yl]-5-ethynyloxolane-3,4-diol;

C. Preparation of Compounds of Formula I, Varying X, $R^1$ and $R^2$

Similarly, following the procedure of 4A above, but replacing [9-((1R,2R,4R,5R)-4-ethynyl-7,7-dimethyl-3,6,8-trioxabicyclo[3.3.0]oct-2-yl)purin-6-yl]cyclopentylamine with other compounds of formula (5), other compounds of Formula I are prepared.

EXAMPLE 5

Preparation of a Compound of Formula (6)

A. Preparation of a Compound of Formula (6) where $R^1$ is Cyclopentyl, $R^2$ is Hydrogen, $R^3$ is 2-Trifluoromethylphenyl, Y is a Covalent Bond, and Z is —C≡C—

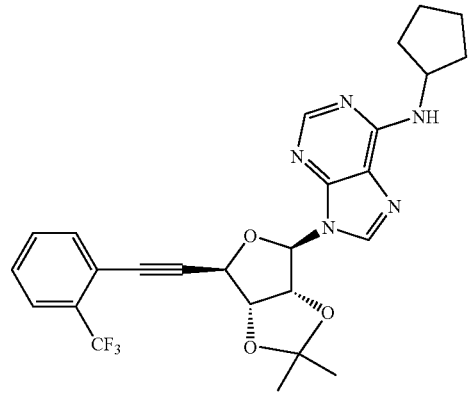

To a solution of [9-((1R,2R,4R,5R)-4-ethynyl-7,7-dimethyl-3,6,8-trioxabicyclo[3.3.0]oct-2-yl)purin-6-yl]cyclopentylamine (40 mg, 0.12 mmol), a compound of formula (5), in tetrahydrofuran (4 ml) under nitrogen was added catalytic amounts (3 mg) of dichlorobis(triphenylphosphine)palladium(II) and copper(II)iodide, followed by 1-iodo-2-trifluoromethylbenzene (0.25 ml, 0.3 mmol). Triethylamine (0.4 ml) was then added, and the mixture stirred for 15 minutes at room temperature. The solvent was removed under reduced pressure, and the residue was purified by preparative TLC, eluting with methanol:methylene chloride (6.5:1), to yield [9-((1R,2R,4R,5R)-7,7-dimethyl-4-{2-[2-(trifluoromethyl)-phenyl]ethynyl}-3,6,8-trioxabicyclo[3.3.0]oct-2-yl)purin-6-yl]cyclopentylamine, a compound of formula (6).

B. Preparation of a Compound of Formula (6) where $R^1$ is Cyclopentyl or Tetrahydrofuran-3-yl, $R^2$, $R^4$ and $R^5$ are Hydrogen, X, $X^1$ and Y are Covalent Bonds, and Z is —C≡C—, varying $R^3$ Similarly, following the procedure of 5A above, but replacing [9-((1R,2R,4R,5R)-4-ethynyl-7,7-dimethyl-3,6,8-trioxabicyclo[3.3.0]oct-2-yl)purin-6-yl]cyclopentylamine with the appropriate compounds of formula (5), the following compounds of formula (6) were prepared:

[9-((1R,2R,4R,5R)-7,7-dimethyl-4-{2-[2-(trifluoromethyl)phenyl]ethynyl}-3,6,8-trioxabicyclo[3.3.0]oct-2-yl)purin-6-yl]oxolan-3-ylamine;

[9-((1R,2R,4R,5R)-7,7-dimethyl-4-{2-[2-fluorophenyl]ethynyl}-3,6,8-trioxabicyclo[3.3.0]oct-2-yl)purin-6-yl]oxolan-3-ylamine;

[9-((1R,2R,4R,5R)-7,7-dimethyl-4-{2-[2-chlorophenyl]ethynyl}-3,6,8-trioxabicyclo[3.3.0]oct-2-yl)purin-6-yl]oxolan-3-ylamine;

[9-((1R,2R,4R,5R)-7,7-dimethyl-4-{2-[thien-2-yl]ethynyl}-3,6,8-trioxabicyclo[3.3.0]oct-2-yl)purin-6-yl]oxolan-3-ylamine;

[9-((1R,2R,4R,5R)-7,7-dimethyl-4-{2-[2-chlorophenyl]ethynyl}-3,6,8-trioxabicyclo[3.3.0]oct-2-yl)purin-6-yl]cyclopentylamine; and {9-[(1R,2R,4R,5R)-7,7-dimethyl-4-(2-(2-thienyl)ethynyl)-3,6,8-trioxabicyclo[3.3.0]oct-2-yl]purin-6-yl}cyclopentylamine.

C. Preparation of a Compound of Formula (6), Varying $R^1$, $R^2$, $R^3$, $R^4$, $R^5$, X, $X^1$ and Y, and Z is —C≡C—

Similarly, following the procedure of 5A above, but optionally replacing [9-((1R,2R,4R,5R)-4-ethynyl-7,7-dimethyl-3,6,8-trioxabicyclo[3.3.0]oct-2-yl)purin-6-yl]cyclopentylamine with other compounds of formula (5), and optionally replacing 1-iodo-2-trifluoromethylbenzene with other compounds of formula $R^3$Y-LG, where LG is a leaving group, the following compounds of Formula I are prepared:

[9-((1R,2R,4R,5R)-7,7-dimethyl-4-{2-[2-methylphenyl]ethynyl}-3,6,8-trioxabicyclo[3.3.0]oct-2-yl)purin-6-yl]cyclopentylamine;

[9-((1R,2R,4R,5R)-7,7-dimethyl-4-{2-[2-fluorophenyl]ethynyl}-3,6,8-trioxabicyclo[3.3.0]oct-2-yl)purin-6-yl]cyclopentylamine;

[9-((1R,2R,4R,5R)-7,7-dimethyl-4-{2-[phenylethynyl]-3,6,8-trioxabicyclo[3.3.0]oct-2-yl)purin-6-yl]cyclopentylamine;

[9-((1R,2R,4R,5R)-7,7-dimethyl-4-{2-[5-chlorothien-2-yl]ethynyl}-3,6,8-trioxabicyclo[3.3.0]oct-2-yl)purin-6-yl]cyclopentylamine;

[9-((1R,2R,4R,5R)-7,7-dimethyl-4-{2-[4-methylisoxazol-3-yl]ethynyl}-3,6,8-trioxabicyclo[3.3.0]oct-2-yl)purin-6-yl]cyclopentylamine;

[9-((1R,2R,4R,5R)-7,7-dimethyl-4-{2-[3,5-dimethylisoxazol-4-yl]ethynyl}-3,6,8-trioxabicyclo[3.3.0]oct-2-yl)purin-6-yl]cyclopentylamine;

[9-((1R,2R,4R,5R)-7,7-dimethyl-4-{2-[cyclopentyl]ethynyl}-3,6,8-trioxabicyclo[3.3.0]oct-2-yl)purin-6-yl]cyclopentylamine;

[9-((1R,2R,4R,5R)-7,7-dimethyl-4-{2-[2-fluorocyclohexyl]ethynyl}-3,6,8-trioxabicyclo[3.3.0]oct-2-yl)purin-6-yl]cyclopentylamine;

[9-((1R,2R,4R,5R)-7,7-dimethyl-4-{2-[piperidin-2-yl]ethynyl}-3,6,8-trioxabicyclo[3.3.0]oct-2-yl)purin-6-yl]cyclopentylamine;

[9-((1R,2R,4R,5R)-7,7-dimethyl-4-{2-[4-methylpiperazin-1-yl]ethynyl}-3,6,8-trioxabicyclo[3.3.0]oct-2-trioxabicyclo[3.3.0]oct-2-yl)purin-6-yl]cyclopentylamine;

[9-((1R,2R,4R,5R)-7,7-dimethyl-4-{2-[pyridin-2-yl]ethynyl}-3,6,8-trioxabicyclo[3.3.0]oct-2-yl)purin-6-yl]cyclopentylamine;

[9-((1R,2R,4R,5R)-7,7-dimethyl-4-{2-[6-fluoropyridin-2-yl]ethynyl}-3,6,8-trioxabicyclo[3.3.0]oct-2-yl)purin-6-yl]cyclopentylamine;

[9-((1R,2R,4R,5R)-7,7-dimethyl-4-{2-[thiazol-2-yl]ethynyl}-3,6,8-trioxabicyclo[3.3.0]oct-2-yl)purin-6-yl]cyclopentylamine;

[9-((1R,2R,4R,5R)-7,7-dimethyl-4-{2-[pyrimidin-2-yl]ethynyl}-3,6,8-trioxabicyclo[3.3.0]oct-2-yl)purin-6-yl]cyclopentylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl]cyclopentylmethylamine;

[9-((1R,2R,4R,5R)-2-trifluoromethyl-7,7-dimethyl-4-{2-[2-fluorophenyl]ethynyl-3,6,8-trioxabicyclo[3.3.0]oct-2-yl-purin-6-yl]cyclopentylmethylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl]cyclobutylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl]cyclohexylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl](2-fluorocyclohexyl)amine;

[9-((1R,2R,4R,5R)-7,7-dimethyl-4-{2-[2-fluorophenyl]ethynyl-3,6,8-trioxabicyclo[3.3.0]oct-2-yl-purin-6-yl]cyclohexylmethylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl](3-fluorocyclopentylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl](4-trifluoromethylcyclopentylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl](3-methoxycyclopentylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl]phenylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl](4-fluorophenyl)amine;

[9-((1R,2R,4R,5R)-7,7-dimethyl-4-{2-[2-fluorophenyl]ethynyl-3,6,8-trioxabicyclo[3.3.0]oct-2-yl-purin-6-yl]benzylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl]pyridin-3-ylamine;

[9-((1R,2R,4R,5R)-7,7-dimethyl-4-{2-[2-fluorophenyl]ethynyl-3,6,8-trioxabicyclo[3.3.0]oct-2-yl-purin-6-yl]thiazol-2-ylamine; and

[9-((1R,2R,4R,5R)-7,7-dimethyl-4-{2-[thien-2-yl]ethynyl}-3,6,8-trioxabicyclo[3.3.0]oct-2-yl)purin-6-yl](5-fluorooxolan-3-ylamine).

D. Preparation of Compounds of Formula I, Varying X $R^1$ and $R^2$

Similarly, following the procedure of 5A above, but optionally replacing [9-((1R,2R,4R,5R)-4-ethynyl-7,7-dimethyl-3,6,8-trioxabicyclo[3.3 .0]oct-2-yl)purin-6-yl]cyclopentylamine with other compounds of formula (5), and optionally replacing 1-iodo-2-trifluoromethylbenzene with other compounds of formula $R^3$Y-LG, where LG is a leaving group, other compounds of Formula I are prepared.

EXAMPLE 6

Preparation of a Compound of Formula I

A. Preparation of a Compound of Formula I where $R^1$ is Cyclopentyl $R^2$, $R^4$ and $R^5$ are Hydrogen $R^3$ is 2-Trifluoromethylphenyl, X, $X^1$ and Y are Covalent Bonds, and Z is —C≡C—

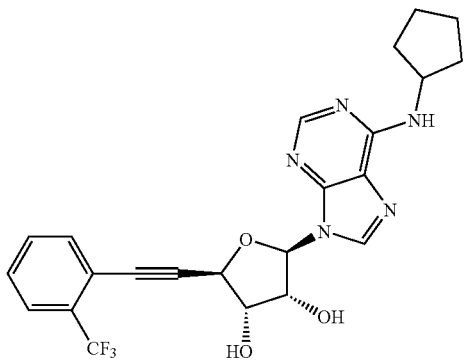

a) To a solution of (4S,2R,3R,5R)-2-[6-(cyclopentylamino)purin-9-yl]-5-ethynyloxolane-3,4-diol (40 mg, 0.12 mmol) in tetrahydrofuran (4 mL) under nitrogen was added catalytic amounts (3 mg) of (4S,2R,3R,5R)-2-[6-(cyclopentylamino)purin-9-yl]-5-ethynyloxolane-3,4-diol (II) and copper (I) iodide, followed by 1-iodo-2-trifluoromethylbenzene (0.042 mL). Triethylamine (0.4 mL) was then added, and the mixture was stirred for 15 minutes at room temperature. The solvent was removed under reduced pressure, and the residue was purified by preparative TLC, eluting with methanol:methylene chloride (6.5:1), to yield (4S,2R,3R,5R)-2-[6-(cyclopentylamino)purin-9-yl]-5-{2-[2-(trifluoromethyl)phenyl]ethynyl}-oxolane-3,4-diol, a compound of Formula I.

b) Alternatively, the acetonide protecting group was removed from [9-((1R,2R,4R,5R)-7,7-dimethyl-4-{2-[2-(trifluoromethyl)-phenyl]ethynyl}-3,6,8-trioxabicyclo[3.3.0]oct-2-yl)purin-6-yl]cyclopentylamine, a compound of formula (6), in the same manner as shown in Example 4 to provide (4S,2R,3R,5R)-2-[6-(cyclopentylamino)purin-9-yl]-5-{2-[2-(trifluoromethyl)phenyl]ethynyl}oxolane-3,4-diol, a compound of Formula I.

B. Preparation of a Compound of Formula I where $R^1$ is Cyclopentyl or Tetrahydrofuran-3-yl, $R^2$, $R^4$ and $R^5$ are Hydrogen, X, $X^1$ and Y are Covalent Bonds, and Z is —C≡C—, Varying $R^3$ Similarly, following the procedure of 6A(a) above, but optionally replacing (4S,2R,3R,5R)-2-[6-(cyclopentylamino)purin-9-yl]-5-ethynyloxolane-3,4-diol with other compounds of Formula I in which $R^3$ is hydrogen, and optionally replacing 1-iodo-2-trifluoromethylbenzene with other compounds of formula $R^3$Y-LG, where LG is a leaving group, or:

Following the procedure of 6A(b) above, but replacing [9-((1R,2R,4R,5R)-7,7-dimethyl-4-{2-[2-(trifluoromethyl)-phenyl]ethynyl}-3,6,8-trioxabicyclo[3.3.0]oct-2-yl)purin-6-yl]cyclopentylamine with other compounds of formula (6);

the following compounds of Formula I were prepared:
(4S,2R,3R,5R)-2-[6-(cyclopentylamino)purin-9-yl]-5-{2-[2-fluorophenyl]-ethynyl}oxolane-3,4-diol;
(4S,2R,3R,5R)-2-[6-(oxalan-3-ylamino)purin-9-yl]-5-{2-[2-(trifluoromethyl)phenyl]-ethynyl}oxolane-3,4-ethynyl}oxolane-3,4-diol;
(4S,2R,3R,5R)-2-[6-(oxalan-3-ylamino)purin-9-yl]-5-{2-[2-fluorophenyl]ethynyl}oxolane-3,4-diol;
(4S,2R,3R,5R)-2-[6-(oxalan-3-ylamino)purin-9-yl]-5-{2-[2-chlorophenyl]ethynyl}oxolane-3,4-diol;
(4S,2R,3R,5R)-2-[6-(oxalan-3-ylamino)purin-9-yl]-5-{2-[thien-2-yl]ethynyl}oxolane-3,4-diol; and
(4S,2R,3R,5R)-2-[6-cyclopentylamino)purin-9-yl]-5-{2-[thien-2-yl]ethynyl}oxolane-3,4-diol;

C. Preparation of a Compound of Formula I Varying $R^1$ $R^2$, $R^3$, $R^4$, $R^5$, X, $X^1$ and Y, and Z is —C≡C—

Similarly, following the procedure of 6A(a) above, but optionally replacing (4S,2R,3R,5R)-2-[6-(cyclopentylamino)purin-9-yl]-5-ethynyloxolane-3,4-diol with other compounds of Formula I in which $R^3$ is hydrogen, and optionally replacing 1-iodo-2-trifluoromethylbenzene with other compounds of formula $R^3$Y-LG, where LG is a leaving group, or:

Following the procedure of 6A(b) above, but replacing [9-((1R,2R,4R,5R)-7,7-dimethyl-4-{2-[2-(trifluoromethyl)-phenyl]ethynyl}-3,6,8-trioxabicyclo[3.3.0]oct-2-yl)purin-6-yl]cyclopentylamine with other compounds of formula (6);

the following compounds of Formula I are prepared:
(4S,2R,3R,5R)-2-[6-cyclopentylamino)purin-9-yl]-5-{2-[phenyl]ethynyl}oxolane-3,4-diol;
(4S,2R,3R,5R)-2-[6-cyclopentylamino)purin-9-yl]-5-{2-[2-chlorophenyl]ethynyl}oxolane-3,4-diol;
(4S,2R,3R,5R)-2-[6-cyclopentylamino)purin-9-yl]-5-{2-[2-methylphenyl]ethynyl}oxolane-3,4-diol;
(4S,2R,3R,5R)-2-[6-cyclopentylarnino)purin-9-yl]-5-{5-chlorothien-2-yl]ethynyl}oxolane-3,4-diol;
(4S,2R,3R,5R)-2-[6-cyclopentylamino)purin-9-yl]-5-{2-[4-methylisoxazol-3-yl]ethynyl}oxolane-3,4-diol;
(4S,2R,3R,5R)-2-[6-cyclopentylamino)purin-9-yl]-5-{2-[2,5-dimethylisoxazol-4-yl]ethynyl}oxolane-3,4-diol;
(4S,2R,3R,5R)-2-[6-cyclopentylamino)purin-9-yl]-5-{2-[cyclopentyl]ethynyl}oxolane-3,4-diol;
(4S,2R,3R,5R)-2-[6-cyclopentylamino)purin-9-yl]-5-{2-[2-fluorocyclohexyl]ethynyl}oxolane-3,4-diol;
(4S,2R,3R,5R)-2-[6-cyclopentylamino)purin-9-yl]-5-{2-[piperidin-2-yl]ethynyl}oxolane-3,4-diol;
(4S,2R,3R,5R)-2-[6-cyclopentylamino)purin-9-yl]-5-{2-[4-methylpiperazin-1-yl]ethynyl}oxolane-3,4-diol;
(4S,2R,3R,5R)-2-[6-cyclopentylamino)purin-9-yl]-5-{2-[pyridin-2-yl]ethynyl}oxolane-3,4-diol;
(4S,2R,3R,5R)-2-[6-cyclopentylamino)purin-9-yl]-5-{2-[6-fluoropyridin-2-yl]ethynyl}oxolane-3,4-diol;
(4S,2R,3R,5R)-2-[6-cyclopentylamino)purin-9-yl]-5-{2-[thiazol-2-yl]ethynyl}oxolane-3,4-diol;
(4S,2R,3R,5R)-2-[6-cyclopentylamino)purin-9-yl]-5-{2-[pyrimidin-2-yl]ethynyl}oxolane-3,4-diol;
(4S,2R,3R,5R)-2-[6-cyclopentylmethylamino)purin-9-yl]-5-{2-[2-fluorophenyl]ethynyl}oxolane-3,4-diol;
(4S,2R,3R,5R)-2-[6-(cyclopentylmethylamino)purin-9-yl]-5-{2-[2-fluorophenyl]-ethynyl}oxolane-3,4-diol;
(4S,2R,3R,5R)-2-[6-(cyclobutylamino)purin-9-yl]-5-{2-[2-fluorophenyl]-ethynyl}oxolane-3,4-diol;
(4S,2R,3R,5R)-2-[6-(cyclohexylamino)purin-9-yl]-5-{2-[2-fluorophenyl]-ethynyl}oxolane-3,4-diol;
(4S,2R,3R,5R)-2-[6-(2-fluorocyclohexylamino)purin-9-yl]-5-{2-[2-fluorophenyl]-ethynyl}oxolane-3,4-diol;
(4S,2R,3R,5R)-2-[6-(cyclohexylmethylamino)purin-9-yl]-5-{2-[2-fluorophenyl]-ethynyl}oxolane-3,4-diol;

(4S,2R,3R,5R)-2-[6-(3-fluorocyclopentylamino)purin-9-yl]-5-{2-[2-fluorophenyl]-ethynyl}oxolane-3,4-diol;
(4S,2R,3R,5R)-2-[6-(4-trifluoromethylcyclopentylamino)purin-9-yl]-5-{2-[2-fluorophenyl]-ethynyl}oxolane-3,4-diol;
(4S,2R,3R,5R)-2-[6-(3-methoxycyclopentylamino)purin-9-yl]-5-{2-[2-fluorophenyl]-ethynyl}oxolane-3,4-diol;
(4S,2R,3R,5R)-2-[6-(phenylamino)purin-9-yl]-5-{2-[2-fluorophenyl]-ethynyl}oxolane-3,4-diol;
(4S,2R,3R,5R)-2-[6-(4-fluorophenylamino)purin-9-yl]-5-{2-[2-fluorophenyl]-ethynyl}oxolane-3,4-diol;
(4S,2R,3R,5R)-2-[6-(benzylamino)purin-9-yl]-5-{2-[2-fluorophenyl]-ethynyl}oxolane-3,4-diol;
(4S,2R,3R,5R)-2-[6-(pyridin-3-ylamino)purin-9-yl]-5-{2-[2-fluorophenyl]-ethynyl}oxolane-3,4-diol;
(4S,2R,3R,5R)-2-[6-(thiazol-2-ylamino)purin-9-yl]-5-{2-[2-fluorophenyl]-ethynyl}oxolane-3,4-diol;
(4S,2R,3R,5R)-2-[6-(oxolan-3-ylmethylamino)purin-9-yl]-5-{2-[2-fluorophenyl]-ethynyl}oxolane-3,4-diol;
(4S,2R,3R,5R)-2-[6-(5-fluorooxolan-3-ylamino)purin-9-yl]-5-{2-[2-fluorophenyl]-ethynyl}oxolane-3,4-diol.

D. Preparation of a Compound of Formula I Varying $R^1$ $R^2$, $R^3$, $R^4$, $R^5$, X, $X^1$ and Y, and Z is —C≡C—

Similarly, following the procedure of 6A above, but replacing [9-((1R,2R,4R,5R)-7,7-dimethyl-4-{2-[2-(trifluoromethyl)-phenyl]ethynyl}-3,6,8-trioxabicyclo[3.3.0]oct-2-yl)purin-6-yl]cyclopentylamine with other compounds of formula (6), other compounds of Formula I are prepared.

EXAMPLE 7

Preparation of a Compound of Formula (7)

Preparation of a Compound of Formula (7) where $R^1$ is Tetrahydrofuran-3-yl, $R^2$ is Hydrogen, $R^3$ is 4-Fluorophenyl, X and Y are Covalent Bonds, and Z is —CH=CH—

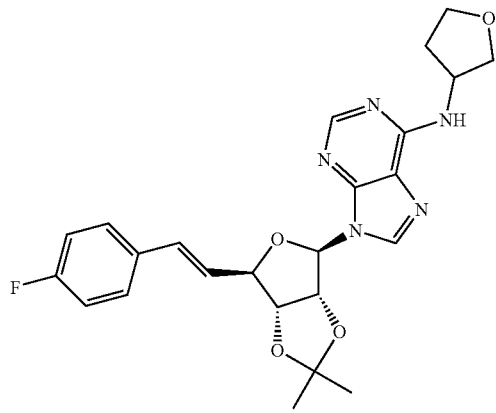

To a solution of (2S,1R,4R,5R)-7,7-dimethyl-3,6,8-trioxa-4-[6-(oxolan-3-ylamino)purin-9-yl]bicyclo[3.3.0]octane-2-carbaldehyde, a compound of formula (4) (200 mg), in methylene chloride (5 ml) was added (4-fluorophenyl) triphenylphosphonium bromide (459 mg, 1 mmol), followed by dropwise addition of an aqueous solution of 50% sodium hydroxide. After addition was complete, the mixture was stirred for 2 hours, then washed with water. The organic layer was separated, dried, and solvent removed under reduced pressure. The residue was purified by preparative thin layer chromatography, eluting with ethyl acetate, to give pure (9-{4-[2-(4-fluorophenyl)vinyl](1R,2R,4R,5R)-7,7-dimethyl-3,6,8-trioxabicyclo[3.3.0]oct-2-yl}purin-6-yl)oxolan-3-ylamine, a compound of formula (7).

B. Preparation of a Compound of Formula (7) where $R^1$ is Cyclopentyl or Tetrahydrofuran-3-yl, $R^2$, $R^4$ and $R^5$ are Hydrogen, X, $X^1$ and Y are Covalent Bonds, and Z is —CH=CH—, Varying $R^3$ Similarly, following the procedure of 7A above, but optionally replacing (2S,1R,4R,5R)-7,7-dimethyl-3,6,8-trioxa-4-[6-(oxolan-3-ylamino)purin-9-yl]bicyclo[3.3.0]octane-2-carbaldehyde with other compounds of formula (4), and optionally replacing (4-fluorophenyl)triphenylphosphonium bromide with other compounds of formula $R^3YCH_2P(PH)_3Br$, the following compounds of formula (7) were prepared:
(9-{4-[2-(5-chlorothien-2-yl)vinyl](1R,2R,4R,5R)-7,7-dimethyl-3,6,8-trioxabicyclo[3.3.0]oct-2-yl}purin-6-yl)cyclopentylamine;
(9-{4-[2-(3,5-dimethylisoxazol-4-yl]vinyl(1R,2R,4R,5R)-7,7-dimethyl-3,6,8-trioxabicyclo[3.3.0]oct-2-yl}purin-6-yl)cyclopentylamine;
(9-{4-[2-(4-methylisoxazol-3-yl]vinyl(1R,2R,4R,5R)-7,7-dimethyl-3,6,8-trioxabicyclo[3.3.0]oct-2-yl}purin-6-yl)cyclopentylamine;
(9-{4-[2-(2-methylphenyl]vinyl(1R,2R,4R,5R)-7,7-dimethyl-3,6,8-trioxabicyclo[3.3.0]oct-2-yl}purin-6-yl)cyclopentylamine; and
(9-{4-[2-(phenyl]vinyl(1R,2R,4R,5R)-7,7-dimethyl-3,6,8-trioxabicyclo[3.3.0]oct-2-yl}purin-6-yl)cyclopentylamine.

C. Preparation of a Compound of Formula (7) Varying $R^1$, $R^2$, $R^3$, $R^4$, $R^5$, X, $X^1$, Y, and Z is —CH=CH—

Similarly, following the procedure of 7A above, but optionally replacing (2S,1R,4R,5R)-7,7-dimethyl-3,6,8-trioxa-4-[6-(oxolan-3-ylamino)purin-9-yl]bicyclo[3.3.0]octane-2-carbaldehyde with other compounds of formula (4), and optionally replacing (4-fluorophenyl)triphenylphosphonium bromide with other compounds of formula $R^3YCH_2P(PH)_3Br$, the following compounds of Formula I are prepared:
(9-{4-[2-(2-methylphenyl]vinyl(1R,2R,4R,5R)-7,7-dimethyl-3,6,8-trioxabicyclo[3.3.0]oct-2-yl}purin-6-yl)cyclopentylamine;
(9-{4-[2-(2-fluorophenyl]vinyl(1R,2R,4R,5R)-7,7-dimethyl-3,6,8-trioxabicyclo[3.3.0]oct-2-yl}purin-6-yl)cyclopentylamine;
(9-{4-[2-(phenyl]vinyl(1R,2R,4R,5R)-7,7-dimethyl-3,6,8-trioxabicyclo[3.3.0]oct-2-yl}purin-6-yl)cyclopentylamine;
(9-{4-[2-(cyclopentyl]vinyl(1R,2R,4R,5R)-7,7-dimethyl-3,6,8-trioxabicyclo[3.3.0]oct-2-yl}purin-6-yl)cyclopentylamine;
(9-{4-[2-(2-fluorocyclohexyl]vinyl(1R,2R,4R,5R)-7,7-dimethyl-3,6,8-trioxabicyclo[3.3.0]oct-2-yl}purin-6-yl)cyclopentylamine;
(9-{4-[2-(piperidin-2-yl]vinyl(1R,2R,4R,5R)-7,7-dimethyl-3,6,8-trioxabicyclo[3.3.0]oct-2-yl}purin-6-yl)cyclopentylamine;
(9-{4-[2-(4-methylpiperazin-1-yl]vinyl(1R,2R,4R,5R)-7,7-dimethyl-3,6,8-trioxabicyclo[3.3.0]oct-2-yl}purin-6-yl)cyclopentylamine;
(9-{4-[2-(pyridin-2-yl]vinyl(1R,2R,4R,5R)-7,7-dimethyl-3,6,8-trioxabicyclo[3.3.0]oct-2-yl}purin-6-yl)cyclopentylamine;

(9-{4-[2-(6-fluoropyridin-2-yl]vinyl(1R,2R,4R,5R)-7,7-dimethyl-3,6,8-trioxabicyclo[3.3.0]oct-2-yl}purin-6-yl)cyclopentylamine;

(9-{4-[2-(thiazol-2-yl]vinyl(1R,2R,4R,5R)-7,7-dimethyl-3,6,8-trioxabicyclo[3.3.0]oct-2-yl}purin-6-yl)cyclopentylamine;

(9-{4-[2-(pyrimidin-2-yl]vinyl(1R,2R,4R,5R)-7,7-dimethyl-3,6,8-trioxabicyclo[3.3.0]oct-2-yl}purin-6-yl)cyclopentylamine;

(9-{4-[2-(2-fluorophenyl)vinyl](1R,2R,4R,5R)-7,7-dimethyl-3,6,8-trioxabicyclo[3.3.0]oct-2-yl}purin-6-yl)cyclopentylmethylamine;

(9-{4-[2-(2-fluorophenyl)vinyl](1R,2R,4R,5R)-7,7-dimethyl-2-trifluoromethyl-3,6,8-trioxabicyclo[3.3.0]oct-2-yl}purin-6-yl)cyclopentylmethylamine;

(9-{4-[2-(2-fluorophenyl)vinyl](1R,2R,4R,5R)-7,7-dimethyl-3,6,8-trioxabicyclo[3.3.0]oct-2-yl}purin-6-yl)cyclobutylmethylamine;

(9-{4-[2-(2-fluorophenyl)vinyl](1R,2R,4R,5R)-7,7-dimethyl-3,6,8-trioxabicyclo[3.3.0]oct-2-yl}purin-6-yl)cyclohexylamine;

(9-{4-[2-(2-fluorophenyl)vinyl](1R,2R,4R,5R)-7,7-dimethyl-3,6,8-trioxabicyclo[3.3.0]oct-2-yl}purin-6-yl)(2-fluorocyclohexylamine);

(9-{4-[2-(2-fluorophenyl)vinyl](1R,2R,4R,5R)-7,7-dimethyl-3,6,8-trioxabicyclo[3.3.0]oct-2-yl}purin-6-yl)cyclohexylmethylamine;

(9-{4-[2-(2-fluorophenyl)vinyl](1R,2R,4R,5R)-7,7-dimethyl-3,6,8-trioxabicyclo[3.3.0]oct-2-yl}purin-6-yl)(3-fluorocyclopentylamine);

(9-{4-[2-(2-fluorophenyl)vinyl](1R,2R,4R,5R)-7,7-dimethyl-3,6,8-trioxabicyclo[3.3.0]oct-2-yl}purin-6-yl)(4-trifluoromethylcyclopentylamine);

(9-{4-[2-(2-fluorophenyl)vinyl](1R,2R,4R,5R)-7,7-dimethyl-3,6,8-trioxabicyclo[3.3.0]oct-2-yl}purin-6-yl)(3-methoxycyclopentylamine);

(9-{4-[2-(2-fluorophenyl)vinyl](1R,2R,4R,5R)-7,7-dimethyl-3,6,8-trioxabicyclo[3.3.0]oct-2-yl}purin-6-yl)phenylamine;

(9-{4-[2-(2-fluorophenyl)vinyl](1R,2R,4R,5R)-7,7-dimethyl-3,6,8-trioxabicyclo[3.3.0]oct-2-yl}purin-6-yl)(4-fluorophenylamine);

(9-{4-[2-(2-fluorophenyl)vinyl](1R,2R,4R,5R)-7,7-dimethyl-3,6,8-trioxabicycyclo[3.3.0]oct-2-yl}purin-6-yl)benzylamine;

(9-{4-[2-(2-fluorophenyl)vinyl](1R,2R,4R,5R)-7,7-dimethyl-3,6,8-trioxabicycyclo[3.3.0]oct-2-yl}purin-6-yl)pyridin-3-ylamine);

(9-{4-[2-(2-fluorophenyl)vinyl](1R,2R,4R,5R)-7,7-dimethyl-3,6,8-trioxabicyclo[3.3.0]oct-2-yl}purin-6-yl)thiazol-2-ylamine; and (9-{4-[2-(2-fluorophenyl)vinyl](1R,2R,4R,5R)-7,7-dimethyl-3,6,8-trioxabicyclo[3.3.0]oct-2-yl}purin-6-yl)(5-fluorooxolan-3-ylamine).

D. Preparation of a Compound of Formula (7) Varying $R^1$, $R^2$, $R^3$, $R^4$, $R^5$, X, $X^1$ Y, and Z is —CH=CH—

Similarly, following the procedure of 7A above, but optionally replacing (2S,1R,4R,5R)-7,7-dimethyl-3,6,8-trioxa-4-[6-(oxolan-3-ylamino)purin-9-yl]bicyclo[3.3.0]octane-2-carbaldehyde with other compounds of formula (4), and optionally replacing (4-fluorophenyl)triphenylphosphonium bromide with compounds of formula $R^3YCH_2P(PH)_3Br$, other compounds of Formula I are prepared.

EXAMPLE 8

Preparation of a Compound of Formula I

A. Preparation of a Compound of Formula I where $R^1$ is Tetrahydrofuran-3-yl, $R^2$ is Hydrogen, $R^3$ is 4-Fluorophenyl, X and Y are Covalent Bonds, and Z is —CH=CH—

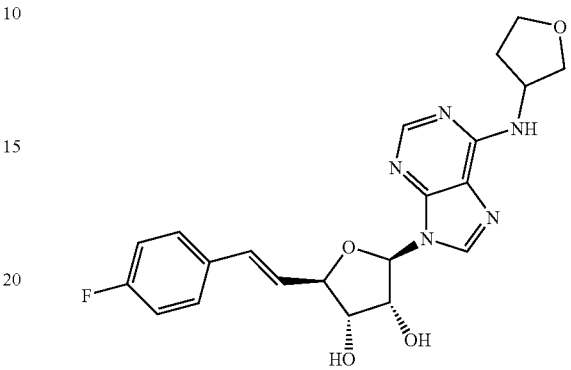

The acetonide protecting group was then removed from (9-{4-[(1E)-2-(4-fluorophenyl)vinyl](1R,2R,4R,5R)-7,7-dimethyl-3,6,8-trioxabicyclo[3.3.0]oct-2-yl}purin-6-yl)oxolan-3-ylamine, a compound of formula (7), in the same manner as shown in Example 4 to provide 5-[2-(4-fluorophenyl)vinyl]-2-[6-(oxolan-3-ylamino)purin-9-yl]oxolane-3,4-diol, a compound of Formula I.

B. Preparation of a Compound of Formula I where $R^1$ is Cyclopentyl or Tetrahydrofuran-3-yl, $R^2$, $R^4$ and $R^5$ are Hydrogen. X, $X^1$ and Y are Covalent Bonds, and Z is —CH=CH—, Varying $R^3$ Similarly, following the procedure of 8A above, but replacing (9-{4-[(1E)-2-(4-fluorophenyl)vinyl](1R,2R,4R,5R)-7,7-dimethyl-3,6,8-trioxabicyclo[3.3.0]oct-2-yl}purin-6-yl)oxolan-3-ylamine with other compounds of formula (7), the following compounds of Formula I were prepared:

5-[(1E)-2-(methoxycarbonylvinyl](4S,2R,3R,5R)-2-[6-(oxolan-3-ylamino)purin-9-yl]oxolane-3,4-diol;

5-[(1E)-2-(2-methylphenyl)vinyl](4S,2R,3R,5R)-2-[6-(oxolan-3-ylamino)purin-9-yl]oxolane-3,4-diol;

5-[2-(5-chlorothien-2-yl)vinyl](4S,2R,3R,5R)-2-[6-(cyclopentylamino)purin-9-yl]oxolane-3,4-diol;

5-[2-(3,5-dimethylisoxazol-4-yl)vinyl](4S,2R,3R,5R)-2-[6-(cyclopentylamino)purin-9-yl]oxolane-3,4-diol;

5-[2-(4-methylisoxazol-3-yl)vinyl](4S,2R,3R,5R)-2-[6-(cyclopentylamino)purin-9-yl]oxolane-3,4-diol;

5-[2-(2-methylphenyl)vinyl](4S,2R,3R,5R)-2-[6-(cyclopentylamino)purin-9-yl]oxolane-3,4-diol; and 5-[2-(phenyl)vinyl](4S,2R,3R,5R)-2-[6-(cyclopentylamino)purin-9-yl]oxolane-3,4-diol;

C. Preparation of a Compound of Formula I Varying $R^1$, $R^2$, $R^3$, $R^4$, $R^5$, X $X^1$, Y, and Z is —CH=CH—

Similarly, following the procedure of 8A above, but replacing (9-{4-[(1E)-2-(4-fluorophenyl)vinyl](1R,2R,4R,5R)-7,7-dimethyl-3,6,8-trioxabicyclo[3.3.0]oct-2-yl}purin-6-yl)oxolan-3-ylamine with other compounds of formula (7), the following compounds of Formula I are prepared:

5-[2-(2-methylphenyl)vinyl](4S,2R,3R,5R)-2-[6-(cyclopentylamino)purin-9-yl]oxolane-3,4-diol, 5-[2-(2-fluorophenyl)vinyl](4S,2R,3R,5R)-2-[6-(cyclopentylamino)purin-9-yl]oxolane-3,4-diol, 5-[2-(phenyl)vinyl](4S,2R,3R,5R)-2-[6-(cyclopentylamino)purin-9-yl]oxolane-3,4-diol, 5-[2-(cyclopentyl)vinyl](4S,2R,3R,5R)-2-[6-(cyclopentylamino)purin-9-yl]oxolane-3,4-diol, 5-[2-(2-fluorocyclohexyl)vinyl](4S,2R,3R,5R)-2-[6-(cyclopentylamino)purin-9-yl]oxolane-3,4-diol, 5-[2-(2-piperidin-2-yl)vinyl](4S,2R,3R,5R)-2-[6-(cyclopentylamino)purin-9-yl]oxolane-3,4-diol, 5-[2-(4-methylpiperazin-1-yl)vinyl](4S,2R,3R,5R)-2-[6-(cyclopentylamino)purin-9-yl]oxolane-3,4-diol, 5-[2-(2-pyridin-2-yl)vinyl](4S,2R,3R,5R)-2-[6-(cyclopentylamino)purin-9-yl]oxolane-3,4-diol, 5-[2-(6-fluoropyridin-2-yl)vinyl](4S,2R,3R,5R)-2-[6-(cyclopentylamino)purin-9-yl]oxolane-3,4-diol, 5-[2-(2-thiazol-2-yl)vinyl](4S,2R,3R,5R)-2-[6-(cyclopentylamino)purin-9-yl]oxolane-3,4-diol, 5-[2-(pyrimidin-2-yl)vinyl](4S,2R,3R,5R)-2-[6-(cyclopentylamino)purin-9-yl]oxolane-3,4-diol, 5-[2-(2-fluorophenyl)vinyl](4S,2R,3R,5R)-2-[6-(cyclopentylmethylamino)purin-9-yl]oxolane-3,4-diol, 5-[2-(2-fluorophenyl)vinyl](4S,2R,3R,5R)-2-[6-(cyclobutylmethylamino)purin-9-yl]oxolane-3,4-diol, 5-[2-(2-fluorophenyl)vinyl](4S,2R,3R,5R)-2-[6-(cyclohexylamino)purin-9-yl]oxolane-3,4-diol, 5-[2-(2-fluorophenyl)vinyl](4S,2R,3R,5R)-2-[6-(2-fluorocyclohexylamino)purin-9-yl]oxolane-3,4-diol, 5-[2-(2-fluorophenyl)vinyl](4S,2R,3R,5R)-2-[6-(2-fluorocyclohexylmethylamino)purin-9-yl]oxolane-3,4-diol, 5-[2-(2-fluorophenyl)vinyl](4S ,2R,3R,5R)-2-[6-(3-fluorocyclopentylamino)purin-9-yl]oxolane-3,4-diol, 5-[2-(2-fluorophenyl)vinyl](4S,2R,3R,5R)-2-[6-(4-trifluoromethylcyclopentylamino)purin-9-yl]oxolane-3,4-diol, 5-[2-(2-fluorophenyl)vinyl](4S,2R,3R,5R)-2-[6-(3-methoxycyclopentylamino)purin-9-yl]oxolane-3,4-diol, 5-[2-(2-fluorophenyl)vinyl](4S,2R,3R,5R)-2-[6-(phenylamino)purin-9-yl]oxolane-3,4-diol, 5-[2-(2-fluorophenyl)vinyl](4S,2R,3R,5R)-2-[6-(benzylamino)purin-9-yl]oxolane-3,4-diol, 5-[2-(2-fluorophenyl)vinyl](4S,2R,3R,5R)-2-[6-(pyridin-3-ylamino)purin-9-yl]oxolane-3,4-diol, 5-[2-(2-fluorophenyl)vinyl](4S,2R,3R,5R)-2-[6-(thiazol-2-ylamino)purin-9-yl]oxolane-3,4-diol, and 5-[2-(2-fluorophenyl)vinyl](4S,2R,3R,5R)-2-[6-(5-fluorooxolan-3-ylamino)purin-9-yl]oxolane-3,4-diol.

D. Preparation of a Compound of Formula I Varying $R^1$, $R^2$, $R^3$, $R^4$, $R^5$, X, $X^1$, Y, and Z is —CH=CH—

Similarly, following the procedure of 8A above, but replacing (9-{4-[(1E)-2-(4-fluorophenyl)vinyl](1R,2R,4R,5R)-7,7-dimethyl-3,6,8-trioxabicyclo[3.3.0]oct-2-yl}purin-6-yl)oxolan-3-ylamine with other compounds of formula (7), other compounds of Formula I are prepared.

EXAMPLE 9

Preparation of a Compound of Formula I

Preparation of a Compound of Formula I where $R^1$ is Tetrahydrofuran-3-yl, $R^2$ is Hydrogen, $R^3$ is 4-Fluorophenyl, X and Y are Covalent Bonds, and Z is —CH$_2$CH$_2$—

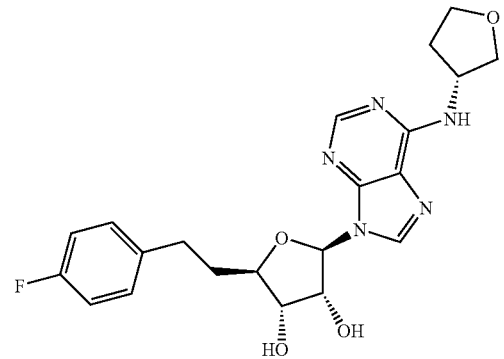

To a solution of 5-[2-(4-fluorophenyl)vinyl](4S,2R,3R,5R)-2-[6-(oxolan-3-ylamino)purin-9-yl]oxolane-3,4-diol (40 mg) in ethanol (5 ml) and cyclohexene (2 ml) was added palladium hydroxide (50 mg), and the mixture was stirred for 24 hours. The catalyst was filtered off, and solvent removed under reduced pressure. The residue was purified by preparative thin layer chromatography, to give pure (4S,2R,3R,5R)-5-[2-(4-fluorophenyl)ethyl]-2-[6-(oxolan-3-ylamino)purin-9-yl]oxolane-3,4-diol, a compound of Formula I.

B. Preparation of a Compound of Formula I where $R^1$ is Cyclopentyl or Tetrahydrofuran-3-yl, $R^2$, $R^4$ and $R^5$ are Hydrogen, X, $X^1$ and Y are Covalent Bonds, and Z is —CH$_2$CH$_2$—, Varying $R^3$ Similarly, following the procedure of 9A above, but replacing 5-[2-(4-fluorophenyl)vinyl](4S,2R,3R,5R)-2-[6-(oxolan-3-ylamino)purin-9-yl]oxolane-3,4-diol with other compounds of Formula I in which Z is —CH=CH—, the following compounds of Formula I were prepared:

(4S,2R,3R,5R)-5-[2-(methoxycarbonyl)ethyl]-2-[6-(oxolan-3-ylamino)purin-9-yl]oxolane-3,4-diol;

(4S,2R,3R,5R)-5-[2-(2-methylphenyl)ethyl]2-[6-(oxolan-3-ylamino)purin-9-yl]oxolane-3,4-diol;

(4S,2R,3R,5R)-5-[2-phenylethyl]2-[6-(cyclopentylamino)purin-9-yl]oxolane-3,4-diol;

(4S,2R,3R,5R)-5-[2-(3,5-dimethylisoxazol-4-yl)ethyl]2-[6-(cyclopentylylamino)purin-9-yl]oxolane-3,4-diol;

(4S,2R,3R,5R)-5-[2-(5-chlorothien-2-yl)ethyl]2-[6-(cyclopentylamino)purin-9-yl]oxolane-3,4-diol.

C. Preparation of a Compound of Formula I Varying $R^1$, $R^2$, $R^3$, $R^4$ and $R^5$ X, $X^1$, Y, and Z is —CH$_2$CH$_2$—

Similarly, following the procedure of 9A above, but replacing 5-[2-(4-fluorophenyl)vinyl](4S,2R,3R,5R)-2-[6-(oxolan-3-ylamino)purin-9-yl]oxolane-3,4-diol with other compounds of Formula I in which Z is —CH=CH—, the following compounds of Formula I are prepared:

(4S,2R,3R,5R)-5-[2-(4-methylisoxazol-3-yl)ethyl]-2-[6-(cyclopentylamino)purin-9-yl]oxolane-3,4-diol;

(4S,2R,3R,5R)-5-[2-(2-methylphenyl)ethyl]-2-[6-(cyclopentylylamino)purin-9-yl]oxolane-3,4-diol;

(4S,2R,3R,5R)-5-[2-(2-methylphenyl)ethyl]-2-[6-(oxolan-3-ylamino)purin-9-yl]oxolane-3,4-diol;

(4S,2R,3R,5R)-5[2-(2-fluorophenyl)ethyl]-2-[6-(cyclopentylamino)purin-9-yl]oxolane-3,4-diol, (4S,2R,3R,5R)-5[2-(phenyl)ethyl]-2-[6-(cyclopentylamino)purin-9-yl]oxolane-3,4-diol, (4S,2R,3R,5R)-5[2-(cyclopentyl)ethyl]-2-[6-(cyclopentylamino)purin-9-yl]oxolane-3,4-diol, (4S,2R,3R,5R)-5[2-(2-fluorocyclohexyl)ethyl]-2-[6-(cyclopentylamino)purin-9-yl]oxolane-3,4-diol, (4S,2R,3R,5R)-5[2-(2-piperidin-2-yl)ethyl]-2-[6-(cyclopentylamino)purin-9-yl]oxolane-3,4-diol, (4S,2R,3R,5R)-5[2-(4-methylpiperazin-1-yl)ethyl]-2-[6-(cyclopentylamino)purin-9-yl]oxolane-3,4-diol, (4S,2R,3R,5R)-5[2-(2-pyridin-2-yl)ethyl]-2-[6-(cyclopentylamino)purin-9-yl]oxolane-3,4-diol, (4S,2R,3R,5R)-5[2-(6-fluoropyridin-2-yl)ethyl]-2-[6-(cyclopentylamino)purin-9-yl]oxolane-3,4-diol, (4S,2R,3R,5R)-5[2-(2-thiazol-2-yl)ethyl]-2-[6-(cyclopentylamino)purin-9-yl]oxolane-3,4-diol, (4S,2R,3R,5R)-5[2-(pyrimidin-2-yl)ethyl]-2-[6-(cyclopentylamino)purin-9-yl]oxolane-3,4-diol, (4S,2R,3R,5R)-5[2-(2-fluorophenyl)ethyl]-2-[6-(cyclopentylmethylamino)purin-9-yl]oxolane-3,4,-diol, (4S,2R,3R,5R)-5[2-(2-fluorophenyl)ethyl]-2-[6-(cyclobutylmethylamino)purin-9-yl]oxolane-3,4,-diol, (4S,2R,3R,5R)-5[2-(2-fluorophenyl)ethyl]-2-[6-(cyclohexylamino)purin-9-yl]oxolane-3,4,-diol, (4S,2R,3R,5R)-5[2-(2-fluorophenyl)ethyl]-2-[6-(2-fluorocyclohexylamino)purin-9-yl]oxolane-3,4,-diol, (4S,2R,3R,5R)-5[2-(2-fluorophenyl)ethyl]-2-[6-(2-fluorocyclohexylmethylamino)purin-9-yl]oxolane-3,4,-diol, (4S,2R,3R,5R)-5[2-(2-fluorophenyl)ethyl]-2-[6-(3-fluorocyclopentylamino)purin-9-yl]oxolane-3,4,-diol, (4S,2R,3R,5R)-5[2-(2-fluorophenyl)ethyl]-2-[6-(4-trifluoromethylcyclopentylamino)purin-9-yl]oxolane-3,4,-diol, (4S,2R,3R,5R)-5[2-(2-fluorophenyl)ethyl]-2-[6-(3-methoxycyclopentylamino)purin-9-yl]oxolane-3,4,-diol, (4S,2R,3R,5R)-5[2-(2-fluorophenyl)ethyl]-2-[6-(phenylamino)purin-9-yl]oxolane-3,4,-diol, (4S,2R,3R,5R)-5[2-(2-fluorophenyl)ethyl]-2-[6-(benzylamino)purin-9-yl]oxolane-3,4,-diol, (4S,2R,3R,5R)-5[2-(2-fluorophenyl)ethyl]-2-[6-(pyridin-3-ylamino)purin-9-yl]oxolane-3,4,-diol, (4S,2R,3R,5R)-5[2-(2-fluorophenyl)ethyl]-2-[6-(thiazol-2-ylamino)purin-9-yl]oxolane-3,4,-diol, and (4S,2R,3R,5R)-5[2-(2-fluorophenyl)ethyl]-2-[6-(5-fluorooxolan-3-ylamino)purin-9-yl]oxolane-3,4-diol.

D. Preparation of a Compound of Formula I Varying $R^1$ $R^2$, $R^3$, $R^4$ and $R^5$, X, $X^1$, Y, and Z is —$CH_2CH_2$—

Similarly, following the procedure of 9A above, but replacing 5-[2-(4-fluorophenyl)vinyl](4S,2R,3R,5R)-2-[6-(oxolan-3-ylamino)purin-9-yl]oxolane-3,4-diol with other compounds of Formula I in which Z is —CH=CH—, other compounds of Formula I are prepared.

EXAMPLE 10

Preparation of a Compound of Formula (8) where $R^1$ is Cyclopentyl and $R^2$ is Hydrogen

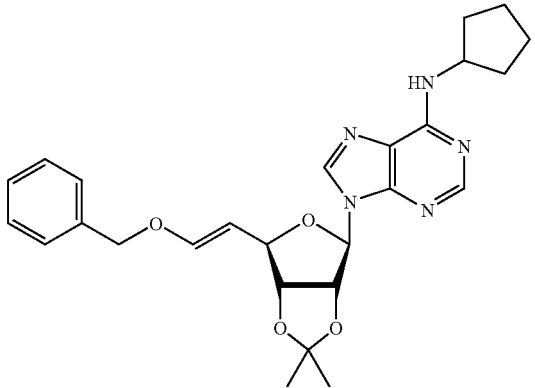

To a stirred solution of benzyloxymethyltriphenyl phosphonium chloride (7.71 g, 18.40 mmol) in tetrahydrofuran (40 mL) was added N-sodiumhexamethyldisilazane (1M in THF, 17.50 mL) dropwise, and the mixture was stirred at −78° C. for 1 hour. Then {(2S,1R,4R)-4-[6-(cyclopentylamino)purin-9-yl]-7,7-dimethyl-3,6,8-trioxabicyclo[3.3.0]oct-2-yl}formaldehyde, a compound of formula (4) (3.73 g, 10 mmol), was dissolved in tetrahydrofuran (10 mL) and added slowly. The mixture was slowly brought to room temperature, and stirred overnight, quenched with $H_2O$ (60 mL) and extracted with ethyl acetate (3×50 mL). The combined organic layers was washed with water (2×50 mL), dried over $Na_2SO_4$, and evaporated under reduced pressure. Column chromatography gave (9-{4-[2-(phenylmethoxy)vinyl](2R,4R,5R)-7,7-dimethyl-3,6,8-trioxabicyclo[3.3.0]oct-2-yl}purin-6-yl)cyclopentylamine, a compound of formula (8).

EXAMPLE 11

Preparation of a Compound of Formula (9) where $R^1$ is Cyclopentyl and $R^2$ is Hydrogen

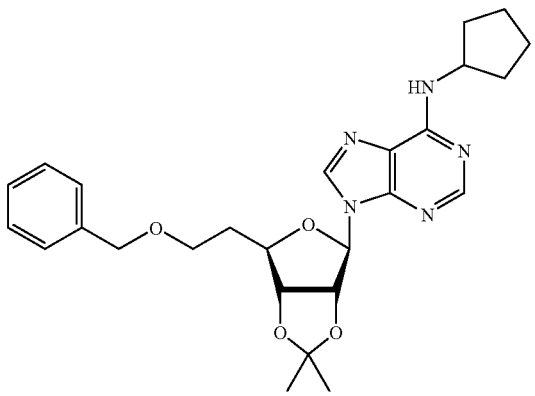

A mixture of (9-{4-[(1E)-2-(phenylmethoxy)vinyl](2R,4R,5R)-7,7-dimethyl-3,6,8-trioxabicyclo[3.3.0]oct-2-yl}purin-6-yl)cyclopentylamine, a compound of formula (8)(1.90 g, 3.98 mmol) and catalytic amount of Pd/C in methanol (30 mL) was stirred under hydrogen (67 psi) overnight. The Pd/C was filtered through celite and washed with methanol. The filtrate was concentrated and the residue, (9-{4-[(1E)-2-(phenylmethoxy)vinyl](2R,4R,5R)-7,7-dimethyl-3,6,8-trioxabicyclo[3.3.0]oct-2-yl}purin-6-yl)cyclopentylamine, a compound of formula (9), was used without further purification.

EXAMPLE 12

Preparation of a Compound of Formula (10) where $R^1$ is cyclopentyl and $R^2$ is Hydrogen

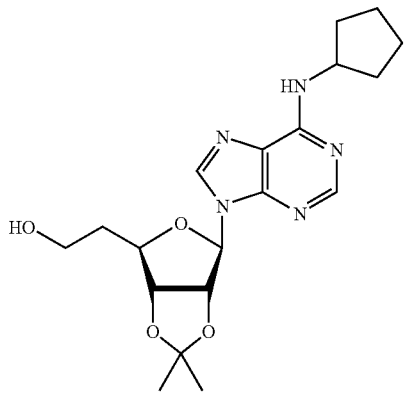

A mixture of (9-{4-[(1E)-2-(phenylmethoxy)vinyl](2R,4R,5R)-7,7-dimethyl-3,6,8-trioxabicyclo[3.3.0]oct-2-yl}purin-6-yl)cyclopentylamine, a compound of formula (9), and Pd(OH)$_2$ in cyclohexene (45 mL) and ethanol (30 mL) was stirred at 80° C. for 5 days. The mixture was filtered through celite and washed with ethanol. The filtrate was concentrated under reduced pressure, and the residue purified by column chromatography to give 2-{(1R,2R,4R)-4-[6-(cyclopentylamino)purin-9-yl]-7,7-dimethyl-3,6,8-trioxabicyclo[3.3.0]oct-2-yl}ethan-1-ol, a compound of the Formula (10).

EXAMPLE 13

Preparation of a Compound of Formula (11) where $R^1$ is cyclopentyl and $R^2$ is Hydrogen

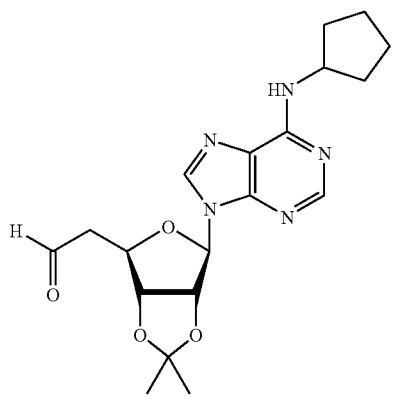

To an ice-cooled solution of 2-{(1R,2R,4R)-4-[6-(cyclopentylamino)purin-9-yl]-7,7-dimethyl-3,6,8-trioxabicyclo[3.3.0]oct-2-yl}ethan-1-ol, a compound of the Formula (10) (0.90 g 2.31 mmol), dicyclohexylcarbodiimide (1.43 g, 6.93 mmol) and pyridine (0.19 mL, 2.31 mmol) in dimethylsulfoxide (16 mL) was added trifluoroacetic acid (0.09 mL, 1.15 mmol) slowly. The resulting mixture was stirred under N$_2$ at room temperature overnight. N,N'-dicyclohexylurea was then filtered off, and washed with ethyl acetate (60 mL). The filtrate was washed with water (3×40 mL), dried over Na$_2$SO$_4$, and concentrated under reduced pressure. The residue, 2-{(1R,2R,4R)-4-[6-(cyclopentylamino)purin-9-yl]-7,7-dimethyl-3,6,8-trioxabicyclo[3.3.0]oct-2-yl}ethan-1-one, a compound of Formula (11) was used without further purification.

EXAMPLE 14

Preparation of a Compound of Formula (12) where $R^1$ is Cyclopentyl and $R^2$ is Hydrogen

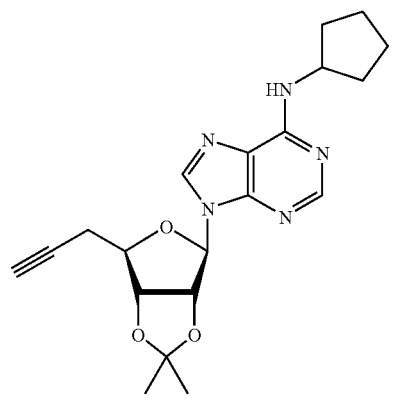

To a stirred solution of potassium-tert-butoxide (0.78 g, 6.93 mmol) in tetrahydrofuran (45 mL) was added (bromomethyl)triphenylphosphonium bromide (1.51 g, 3.27 mmol) in small portions at −78° C. The resulting mixture was stirred at −78° C. for 2 hours. 2-{(1R,2R,4R)-4-[6-(cyclopentylamino)purin-9-yl]-7,7-dimethyl-3,6,8-trioxabicyclo[3.3.0]oct-2-yl}ethan-1-one, a compound of Formula (11) (0.89 g, 2.31 mmol) dissolved in THF (15 mL) was added slowly and the mixture stirred under an atmosphere of $N_2$ at −78° C. for 3 hours, brought to room temperature slowly and stirred for 4 days. The reaction mixture was quenched with saturated $NH_4Cl$ aqueous solution (15 mL) and diluted with $H_2O$ (60 mL), and then extracted with EtOAc (3×50 mL). The combined organic layers were washed with $H_2O$ (2×50 mL), dried over $Na_2SO_4$, and evaporated under reduced pressure, to provide {9-[4-((2E)-3-bromoprop-2-enyl)(2R,4R,5R)-7,7-dimethyl-3,6,8-trioxabicyclo[3.3.0]oct-2-yl]purin-6-yl}cyclopentylamine, a compound of formula (12), which was isolated by column chromatography.

To a stirred solution of {9-[4-((2E)-3-bromoprop-2-enyl)(2R,4R,5R)-7,7-dimethyl-3,6,8-trioxabicyclo[3.3.0]oct-2-yl]purin-6-yl}cyclopentylamine, (0.40 g, 0.86 mmol) in tetrahydrofuran (25 mL) was added potassium-tert-butoxide (0.78 g, 6.93 mmol) in small portions at −78° C. The resulting mixture was stirred at −78° C. for 30 minutes, then brought to room temperature slowly and stirred overnight. The reaction mixture was quenched with saturated aqueous ammonium chloride solution (5 mL) and diluted with $H_2O$ (30 mL), then extracted with EtOAc (3×30 mL). The combined organic layers were washed with water (2×30 mL), dried over sodium sulfate, filtered, and the filtrate evaporated under reduced pressure, to provide [9-((2R,4R,5R)-7,7-dimethyl-3,6,8-trioxa-4-prop-2-ynylbicyclo[3.3.0]oct-2-yl)purin-6-yl]cyclopentylamine, a compound of formula (13), which was isolated by column chromatography.

EXAMPLE 15

Preparation of a Compound of Formula I

Preparation of a Compound of Formula I where $R^1$ is Cyclopentyl, $R^2$ and $R^3$ are Hydrogen, X and Y are Covalent Bonds, $X^1$ is —$CH_2$—and Z is —C≡C—

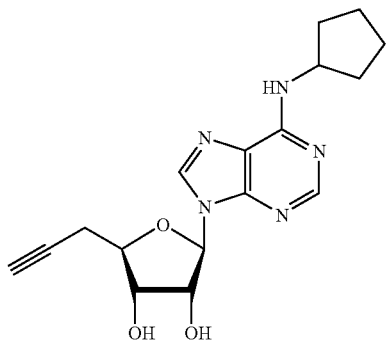

[9-((2R,4R,5R)-7,7-dimethyl-3,6,8-trioxa-4-prop-2-ynylbicyclo[3.3.0]oct-2-yl)purin-6-yl]cyclopentylamine, a compound of formula (13), was stirred in 80% acetic acid aqueous solution (20 mL) at 80° C. in a sealed tube for 2 days. The solvent was removed under reduced pressure, and the residue purified by preparative thin layer chromatography, to give (4S,2R,5R)-2-[6-(cyclopentylamino)purin-9-yl]-5-prop-2-ynyloxolane-3,4-diol, a compound of Formula I.

EXAMPLE 16

Preparation of a Compound of Formula I

A. Preparation of a Compound of Formula I where $R^1$ is Cyclopentyl, $R^2$ is Hydrogen, $R^3$ is 2-Fluorophenyl, X and Y are Covalent Bonds, $X^1$ is —$CH_2$—and Z is —C≡C—

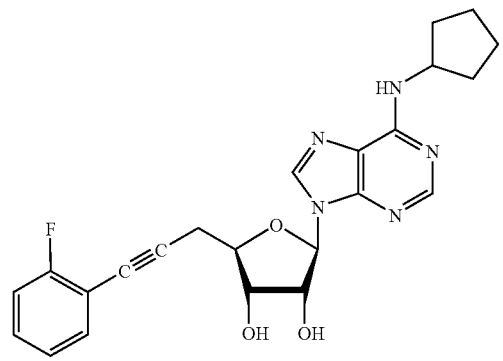

To a stirred solution of (4S,2R,5R)-2-[6-(cyclopentylamino)purin-9-yl]-5-prop-2-ynyloxolane-3,4-diol (0.017 g, 0.05 mmol) and 1-fluoro-2-iodobenzene (0.02 mL, 0.13 mmol) in THF (3.50 mL) under an atmosphere of $N_2$ was added catalytic amount of dichlorobis(triphenylphosphine) palladium (II) and copper (I) iodide. $Et_3N$ (0.20 mL) was then added. The resulting mixture was stirred under $N_2$ at 75° C. for 2 days. The solvent was removed under reduced pressure, and the residue was purified by preparative thin layer chromatography to give (4S,2R,3R,5R)-2-[6-(cyclopentylamino)purin-9-yl]-5-[3-(2-fluorophenyl)prop-2-ynyl]oxolane-3,4-diol, a compound of Formula I.

B. Preparation of a Compound of Formula I where $R^1$ is Cyclopentyl, $R^2$, $R^4$ and $R^5$ are Hydrogen, X and $X^1$ are Covalent Bonds, Y is $CH_2$, and Z is —C≡C—, Varying $R^3$ Similarly, following the procedures of Examples 10–16 above, the following compounds of Formula I in which $X^1$ is —$CH_2$— and Z is —C≡C—, were prepared:

(4S,2R,3R,5R)-2-[6-(cyclopentylamino)purin-9-yl]-5-{3-[2-fluorophenyl]prop-2-ynyl}oxolane-3,4-diol; and (4S,2R,3R,5R)-2-[6-(cyclopentylamino)purin-9-yl]-5-{3-[2-(trifluoromethyl)phenyl]prop-2-ynyl}oxolane-3,4-diol.

C. Preparation of a Compound of Formula I Varying $R^1$, $R^2$, $R^3$, $R^4$ and $R^5$, X, $X^1$ and Y is $CH_2$, and Z is —C≡C—

Similarly, following the procedures of Examples 10–16 above, the following compounds of Formula I in which $X^1$ is —$CH_2$— and Z is —C—C— are prepared:

(4S,2R,3R,5R)-2-[6-(cyclopentylamino)purin-9-yl]-5-{3-[4-methylisoxazol-3-yl]prop-2-ynyl}oxolane-3,4-diol;

(4S,2R,3R,5R)-2-[6-(cyclopentylamino)purin-9-yl]-5-{3-[2-methylphenyl]prop-2-ynyl}oxolane-3,4-diol;

(4S,2R,3R,5R)-2-[6-(oxolan-3-ylamino)purin-9-yl]-5-{3-[2-fluorophenyl]prop-2-ynyl}oxolane-3,4-diol;

(4S,2R,3R,5R)-2-[6-(cyclopentylamino)purin-9-yl]-5-{3-[2-fluorophenyl]prop-2-ynyl}oxolane-3,4-diol;

(4S,2R,3R,5R)-2-[6-(cyclopentylamino)purin-9-yl]-5-{3-[phenyl]prop-2-ynyl}oxolane-3,4-diol;

(4S,2R,3R,5R)-2-[6-(cyclopentylamino)purin-9-yl]-5-{3-[cyclopentyl]prop-2-ynyl}oxolane-3,4-diol;

(4S,2R,3R,5R)-2-[6-(cyclopentylamino)purin-9-yl]-5-{3-[2-fluorocyclohexyl]prop-2-ynyl}oxolane-3,4-diol;

(4S,2R,3R,5R)-2-[6-(cyclopentylamino)purin-9-yl]-5-{3-[piperidin-2-yl]prop-2-ynyl}oxolane-3,4-diol;

(4S,2R,3R,5R)-2-[6-(cyclopentylamino)purin-9-yl]-5-{3-[4-methylpiperazin-1-yl]prop-2-ynyl}oxolane-3,4-diol;

(4S,2R,3R,5R)-2-[6-(cyclopentylamino)purin-9-yl]-5-{3-[pyridin-2-yl]prop-2-ynyl}oxolane-3,4-diol;

(4S,2R,3R,5R)-2-[6-(cyclopentylamino)purin-9-yl]-5-{3-[6-fluoropyridin-2-yl]prop-2-ynyl}oxolane-3,4-diol;

(4S,2R,3R,5R)-2-[6-(cyclopentylamino)purin-9-yl]-5-{3-[thiazol-2-yl]prop-2-ynyl}oxolane-3,4-diol;

(4S,2R,3R,5R)-2-[6-(cyclopentylamino)purin-9-yl]-5-{3-[pyrimidin-2-yl]prop-2-ynyl}oxolane-3,4-diol;

(4S,2R,3R,5R)-2-[6-(cyclopentylmethylamino)purin-9-yl]-5-{3-[2-fluorophenyl]prop-2-ynyl}oxolane-3,4-diol;

(4S,2R,3R,5R)-2-[6-(cyclobutylmethylamino)purin-9-yl]-5-{3-[2-fluorophenyl]prop-2-ynyl}oxolane-3,4-diol;

(4S,2R,3R,5R)-2-[6-(cyclohexylamino)purin-9-yl]-5-{3-[2-fluorophenyl]prop-2-ynyl}oxolane-3,4-diol;

(4S,2R,3R,5R)-2-[6-(2-fluorocyclohexylamino)purin-9-yl]-5-{3-[2-fluorophenyl]prop-2-ynyl}oxolane-3,4-diol;

(4S,2R,3R,5R)-2-[6-(2-fluorocyclohexylmethylamino)purin-9-yl]-5-{3-[2-fluorophenyl]prop-2-ynyl}oxolane-3,4-diol;

(4S,2R,3R,5R)-2-[6-(3-fluorocyclopentylamino)purin-9-yl]-5-{3-[2-fluorophenyl]prop-2-ynyl}oxolane-3,4-diol;

(4S,2R,3R,5R)-2-[6-(4-trifluoromethylcyclopentylamino)purin-9-yl]-5-{3-[2-fluorophenyl]prop-2-ynyl}oxolane-3,4-diol;

(4S,2R,3R,5R)-2-[6-(phenylamino)purin-9-yl]-5-{3-[2-fluorophenyl]prop-2-ynyl}oxolane-3,4-diol;

(4S,2R,3R,5R)-2-[6-(benzylamino)purin-9-yl]-5-{3-[2-fluorophenyl]prop-2-ynyl}oxolane-3,4-diol;

(4S,2R,3R,5R)-2-[6-(pyridin-3-ylamino)purin-9-yl]-5-{3-[2-fluorophenyl]prop-2-ynyl}oxolane-3,4-diol;

(4S,2R,3R,5R)-2-[6-(thiazol-2-ylamino)purin-9-yl]-5-{3-[2-fluorophenyl]prop-2-ynyl}oxolane-3,4-diol; and (4S,2R,3R,5R)-2-[6-(5-fluorooxolan-3-ylamino)purin-9-yl]-5-{3-[2-fluorophenyl]prop-2-ynyl}oxolane-3,4-diol.

D. Preparation of a Compound of Formula I Varying $R^1$, $R^2$, $R^3$, $R^4$ and $R^5$, X, $X^1$ and Y is $CH_2$, and Z is —C≡C—

Similarly, following the procedures of Examples 10–16 above, other compounds of Formula I in which $X^1$ is —$CH_2$— and Z is —C—C— are prepared.

EXAMPLE 17

Preparation of a Compound of Formula I

A. Preparation of a Compound of Formula I where $R^1$ is 2-Hydroxycyclopentyl, $R^2$ is Hydrogen, $R^3$ is Hydrogen, X, $X^1$ and Y are Covalent Bonds, and Z is —C≡C—

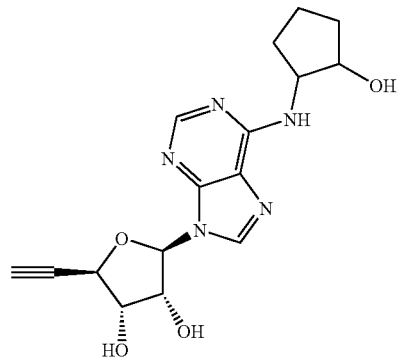

1) To a suspension of potassium t-butoxide (0.84 g, 7.5 mmol) in tetrahydrofuran (5 ml) at −78° C. was added bromomethyltriphenylphosphonium (1.64 g, 3.75 mmol) in small portions, and the mixture stirred for 2 hours. To this mixture was added a solution of (2S,1R,4R,5R)-4-[6-chloropurin-9-yl]-7,7-dimethyl-3,6,8-trioxabicyclo[3.3.0]octane-2-carbaldehyde (1 mmol) in tetrahydrofuran (20 ml), and the mixture was stirred for 2 hours at −78° C. The reaction mixture was then allowed to warm to room temperature and stirred for 24 hours, then quenched with aqueous ammonium chloride, and partitioned between water and ethyl acetate. The organic layer was separated, dried over magnesium sulfate, filtered, and the solvent removed from the filtrate under reduced pressure, to yield (1R,5R,6R,8R)-6-(6-chloropurin-9-yl)-8-ethynyl-3,3-dimethyl-2,4,7-trioxabicyclo[3.3.0]octane.

2) To a solution of (1R,5R,6R,8R)-6-(6-chloropurin-9-yl)-8-ethynyl-3,3-dimethyl-2,4,7-trioxabicyclo[3.3.0]octane (50 mg) and trans 2-aminocyclopentanol (0.04 g) in ethanol was added triethylamine (0.12 ml), and the mixture was stirred at 60° C. for 32 hours. Solvent was then removed under reduced pressure, and the residue dissolved in ethyl acetate, washed with dilute nitric acid, followed by brine, dried over sodium sulfate, filtered, and the solvent removed from the filtrate under reduced pressure, to provide 2-[9-((1R,2R,4R,5R)-4-ethynyl-7,7-dimethyl-3,6,8-trioxabicyclo[3.3.0]oct-2-yl)purin-6-yl]cyclopentan-1-ol.

3) In a sealed tube, 2-[9-((1R,2R,4R,5R)-4-ethynyl-7,7-dimethyl-3,6,8-trioxabicyclo[3.3.0]-oct-2-yl)purin-6-yl]cyclopentan-1-ol was stirred in 10 ml of 80% acetic acid/water overnight. The solvent was then removed under reduced pressure, and the residue purified by preparative thin layer chromatography, eluting with 10% methanol/methylene chloride, to provide (4S,2R,3R,5R)-5-ethynyl-2-{6-[(2-hydroxycyclopentyl)amino]purin-9-yl}oxolane-3,4-diol.

All compounds of Formula I were characterized by nmr spectra and mass spectra. For example:

(4S,2R,3R,5R)-2-[6-(cyclopentylamino)purin-9-yl]-5-ethynyloxolane-3,4-diol:

$^1$H-NMR (CDCl$_3$) 1.54–1.79 (m, 6H), 2.06–2.13 (m, 2H), 3.47 (s, 1H), 4.45–4.58 (m, 2H), 4.71 (s, 1H), 4.94 (s, 1H), 6.01 (d, 1H, J=5.09 Hz), 6.38 (s, 1H, NH), 8.03 (s, 1H), 8.26 (s, 1H). MH$^+$ 317.

(4S,2R,3R,5R)-2-[6-(cyclopentylamino)purin-9-yl]-5-[2-(2-fluorophenyl)ethynyl]oxolane-3,4-diol:

$^1$H-NMR (CDCl$_3$) 1.51–1.77 (m, 6H), 2.08–2.14 (m, 2H), 4.03 (s, 1H, OH), 4.56 (s, 1H, OH), 4.61 (d, 1H, J=4.30 Hz), 4.78–4.81 (m, 1H), 5.21 (s, 1H), 5.94 (d, 1H, J=6.65 Hz), 6.07 (d, 1H, J=5.48 Hz), 6.56 (s, 1H, NH), 7.01–7.07 (m, 2H), 7.26–7.35 (m, 2H), 8.11 (s, 1H) MH$^+$ 412.

EXAMPLE 18

Hard gelatin capsules containing the following ingredients are prepared:
Quantity

| Ingredient | (mg/capsule) |
|---|---|
| Active Ingredient | 30.0 |
| Starch | 305.0 |
| Magnesium stearate | 5.0 |

The above ingredients are mixed and filled into hard gelatin capsules.

EXAMPLE 19

A tablet formula is prepared using the ingredients below:
Quantity

| Ingredient | (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

EXAMPLE 20

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

EXAMPLE 21

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

EXAMPLE 22

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

EXAMPLE 23

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

EXAMPLE 24

A subcutaneous formulation may be prepared as follows:

| Ingredient | Quantity |
| --- | --- |
| Active Ingredient | 5.0 mg |
| Corn Oil | 1.0 mL |

EXAMPLE 25

An injectable preparation is prepared having the following composition:

| Ingredients | Amount |
| --- | --- |
| Active ingredient | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

EXAMPLE 26

A topical preparation is prepared having the following composition:

| Ingredients | grams |
| --- | --- |
| Active ingredient | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

EXAMPLE 27

Sustained Release Composition

| Ingredient | Weight Range (%) | Preferred Range (%) | Most Preferred |
| --- | --- | --- | --- |
| Active ingredient | 50–95 | 70–90 | 75 |
| Microcrystalline cellulose (filler) | 1–35 | 5–15 | 10.6 |
| Methacrylic acid copolymer | 1–35 | 5–12.5 | 10.0 |
| Sodium hydroxide | 0.1–1.0 | 0.2–0.6 | 0.4 |
| Hydroxypropyl methylcellulose | 0.5–5.0 | 1–3 | 2.0 |
| Magnesium stearate | 0.5–5.0 | 1–3 | 2.0 |

The sustained release formulations of this invention are prepared as follows: compound and pH-dependent binder and any optional excipients are intimately mixed(dry-blended). The dry-blended mixture is then granulated in the presence of an aqueous solution of a strong base which is sprayed into the blended powder. The granulate is dried, screened, mixed with optional lubricants (such as talc or magnesium stearate), and compressed into tablets. Preferred aqueous solutions of strong bases are solutions of alkali metal hydroxides, such as sodium or potassium hydroxide, for example sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl. methylcellulose, cationic methacrylate copolymers (dimethylaminoethyl methacrylate/methyl-butyl methacrylate copolymers—Eudragit® E—Röhm. Pharma), and the like. These film-forming agents may optionally contain colorants, plasticizers, and other supplemental ingredients.

The compressed tablets have a hardness sufficient to withstand 8 Kp compression. The tablet size will depend primarily upon the amount of compound in the tablet. The tablets will include from 300 to 1100 mg of compound free base. For example, the tablets will include amounts of compound free base ranging from 400–600 mg, 650–850 mg, and 900–1100 mg.

In order to influence the dissolution rate, the time during which the compound containing powder is wet mixed is controlled. For example the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

EXAMPLE 28

Materials

The $A_1$-adenosine antagonists 8-cyclopentyl-1,3-dipropylxanthine (CPX) and 8-cyclopentyl-1,3-dimethylxanthine (CPT), the $A_1$-adenosine agonists $N_6$-cyclopentyladenosine (CPA), 2-chloro-$N_6$-cyclopentyladenosine (CCPA), and —$N_6$-cyclohexyladenosine (CHA), the adenosine deaminase inhibitor erythro-9-(2-hydroxy-3-nonyl)adenine (EHNA), the adenosine kinase inhibitor iodotubercidin, and forskolin were purchased from Research Biochemicals (Natick, Mass.). {[(5-{6-[(3R)oxolan-3-yl]amino}purin-9-yl)(3S,2R,4R)-3,4-di-hydroxyoxolan-2-yl]-methoxy}-N-methylcarboxamide, molecular weight 394.38, is a derivative of the selective $A_1$-adenosine receptor full agonist CVT-510. Adenosine was purchased from Sigma Chemical (St. Louis, Mo.). The radioligand 8-cyclopentyl-1,3-dipropyl-[2,3-$^3$H (N)]xanthine ([$^3$H]CPX) was purchased from New England Nuclear (Boston, Mass.). Concentrated stock solutions (10–100 mM) of CVT-2759, CPX, CPT, CPA, CCPA, CHA, and forskolin were dissolved in dimethylsulfoxide, stored as aliquots at −80° C., and diluted in physiological saline for use in experiments. The final content of dimethylsulfoxide in saline during experiments was not more than 0.1%. Adenosine and EHNA were dissolved in saline immediately before use.

Binding Assays—DDT$_1$ Cells

Cell Culture

DDT cells (hamster vas deferens smooth muscle cell line) were grown as monolayers in petri dishes using Dulbecco's Modified Eagle's Medium (DMEM) containing 2.5 μg ml$^{-1}$ amphotericin B, 100 U ml$^{-1}$ penicillin G, 0.1 mg ml$^{-1}$ streptomycin sulfate and 5% fetal bovine serum in a humidified atmosphere of 95% air and 5% CO$_2$. Cells were subcultured twice weekly by dispersion in Hank's Balanced Salt Solution (HBSS) without the divalent cations and containing 1 mM EDTA. The cells were then seeded in growth medium at a density of 1.2×10$^5$ cells per plate and experiments were performed 4 days later at approximately one day preconfluence.

Membrane Preparations

Cell layers were washed twice with HBSS (2×10 ml), scraped free of the plate with the aid of a rubber policeman in 5 ml of 50 mM Tris-HCl buffer pH 7.4 at 4° C. and the suspension homogenized for 10 s. The homogenate was centrifuged at 27,000× g for 10 min, resuspended in buffer, and centrifuged again, as described above. The protein content was determined with a Biorad Protein Assay Kit (Richmond, Calif.) using bovine serum albumin as standard. This membrane suspension was stored dimethylsulfoxide (DMSO) in He buffer (10 mM HEPES, 1 uM EDTA at pH 7.4) and stored in liquid nitrogen at −80° C.

Competitive Binding Assays:

Compounds of Formula I were assayed to determine their affinity for the A$_1$ adenosine receptor sites on the membranes of DDT cells. Briefly, 50–70 ug of membrane protein were incubated in a mixture containing 2 U/ml adenosine deaminase, 10 mM GTP-γS in 5 mM HE buffer containing 5 mM MgCl$_2$ in glass tubes. Stock solutions of the compounds of the invention were serially diluted (10$^{-10}$M to 10$^{-4}$M) in HE buffer or HE buffer alone (control to determine non-specific binding) and added to the incubation mixture. Finally, tritiated cyclopentyladenosine ($^3$H-CPA) was added to a final concentration of 1.5 nM. After incubation at 23° C. 90 minutes, the reaction was stopped by filtration on a Brandel MR24 cell harvester and washing with ice-cold Tris-EDTA buffer (three times, approximate volume 10 ml/wash) over Whatman GF/B filters (presoaked for 1 h in 0.3% polyethylenimine to reduce non-specific binding). Filters were transferred to scintillation vials and 5 ml of Scintisafe (VWR, Brisbane, Calif.) was added. The amount of radioactivity retained on the filters was determined by liquid scintillation spectrometry. Protein determinations were by the method of Bradford (1976. Anal. Biochem. 72:248) using bovine serum albumin as the standard.

The compounds of Formula I were shown to be A$_1$-adenosine receptor agonists in this assay.

EXAMPLE 29

[$^{35}$S]GTPγS Binding Assays

The ability of agonists to activate G proteins was determined by using radiolabeled GTP ([$^{35}$S]GTPγS). Briefly, membrane proteins (30–50 μg/assay tube) were placed in glass tubes containing 50 mM Tris-HCl buffer pH 7.4, 5 mM MgCl$_2$, 100 mM NaCl, 1 mM dithiothreitol, 0.2 units ml$^{-1}$ adenosine deaminase, 0.5% BSA, 1 mM EDTA, 10 mM GDP, and 0.3 nM [$^{35}$S]GTPγS. Varying concentrations of the compounds of the invention (putative A$_1$ adenosine receptor agonists), a known A$_1$ adenosine receptor full agonist N cyclopentyladenosine (CPA or CCPA) or a control tube containing 10 μM GTPγS but no agonist (to determine nonspecific binding) were added to separate tubes. The assay tubes were incubated for 90 minutes at 37° C. Agonist stimulated binding was assessed by determining the difference between total binding in the presence of putative agonists and basal binding determined in the absence of CPA. Results were expressed as the percentage stimulation of the putative agonists relative to the full agonist CPA after subtracting out non-specific binding.

The compounds of Formula I were shown to be A$_1$-adenosine receptor agonists in this assay.

EXAMPLE 30

Guinea Pig Isolated Perfused Hearts

Guinea pigs (Hartley) of either sex weighing 300–350 g are anaesthetized with methoxyflurane and killed by decapitation. The chest is cut open, and the heart quickly removed and rinsed in ice-cold modified Krebs-Henseleit (K-H) solution. The contents of the modified K-H solution are (in mM) 117.9 NaCl, 4.8 KCl, 2.5 CaCl$_2$, 1.18 MgSO$_2$, 1.2 KH$_2$PO$_4$, 0.5 Na$_2$ EDTA, 0.14 ascorbic acid, 5.5 dextrose, 2.0 pyruvic acid (sodium salt), and 25 NaHCO$_3$. The K-H solution is continuously gassed with 95% O$_2$–5% CO$_2$, and the pH adjusted to a value of 7.4. To perfuse the heart by the Langendorff method, the transected aorta is put onto a glass cannula and secured by a ligature. Retrograde perfusion of the aorta is initiated immediately at a constant flow of 10 ml/min with modified K-H solution warmed to 36.0±0.5° C. A side port in the cannula is used to connect the perfusion line to a Gould pressure transducer for measurement of coronary perfusion pressure. Coronary perfusion pressure was continuously recorded on a strip chart (Gould RS3400, Cleveland, Ohio) throughout each experiment. Coronary conductance (in ml·min$^{-1}$·mmHg−1) is calculated as the ratio of coronary flow (10 ml/min) to perfusion pressure (in mmHg). To facilitate the exit of fluid from the left ventricle, the leaflets of the mitral valve are trimmed with fine spring-handled scissors. When appropriate, hearts are paced at a constant rate using external electrodes. After completion of dissection and instrumentation, stimulus-to-His bundle (S-H) interval and coronary perfusion pressure is monitored continuously, each heart being allowed to equilibrate for 20–40 min before the administration of drug. Experimental interventions are always preceded and followed by control measurements. Criteria for the exclusion of hearts from the study are 1) a coronary perfusion pressure of <50 mmHg, 2) absence of a stable coronary perfusion pressure during the equilibration period, and 3) inability to pace a heart at a constant rate throughout an experiment.

For electrical pacing of hearts, a bipolar Teflon-coated electrode is placed in the wall of the intra-atrial septum. Parts of the left and right atrial tissues, including the region of the sinoatrial node, are removed, both to decrease the spontaneous heart rate and to expose the atrial septum for electrode placement. Hearts are electrically paced at a fixed rate of 3.2 HZ. Stimuli are provided by an interval generator (model 1830, WPI, Sarasota, Fla.) and delivered through a stimulus isolation unit (model 1880, WPI) as square wave pulses of 3 ms in duration and at least twice the threshold intensity.

S-H interval Prolongation of the S-H interval is used as a measure of the negative dromotropic effect of A$_1$-adenosine agonists on AV nodal conduction. The His bundle electrogram is recorded from a unipolar electrode placed in the right side of the interatrial septum adjacent to the AV junction. The signal is displayed continuously in real time on an oscilloscope screen at a sweep rate of 10 ms/cm. The duration of time from the first pacing artifact to the maximum upward deflection of the His bundle signal is used as the S-H interval.

Hearts are equilibrated until the S-H interval and CPP remains constant. The test compound is used to the perfused line in a final concentration of 0.3, 3, 10 and in some hearts up to 30 μM. If the second degree AV block happens at any concentration before 30 μM, the test compound is withdrawn to washout. After washout of the first test compound, a second test compound could not be used in the same heart unless the SH interval and CPP comes back to the control or S-H interval is prolonged less than 2 ms compared to the control. Up to three compounds can be used in the same heart.

The compounds of Formula I demonstrate the ability to delay AV nodal conduction in this assay.

EXAMPLE 31

Anti-Emesis Studies

For all the experiments adult male ferrets, body weight range 1–1.5 kg, are used. Emesis is induced by X-irradiation, morphine and cisplatin.

X-Irradiation:

The ferrets are weighed on the day before the experiment. On the day of the experiment each ferret receives 2 Gy (200 Rad) whole body X-irradiation, administered over a 5 minute period. The $A_1$ receptor agonists or partial agonists are administered via the subcutaneous route immediately after X-irradiation(i.e. approximately 25 minutes before the onset of emesis). When investigating the effects of the A1 receptor antagonist, DPCPX, on the partial agonist either both compounds are administered simultaneously immediately after X-irradiation, or the DPCPX was given as a 15 minute pre-treatment. In all cases, the ferrets are observed for 2 hours after X-irradiation, and the time and numbers of retches and vomits are recorded.

Morphine:

The ferrets are weighed on the day before the experiment. The adenosine $A_1$ receptor agonist is administered subcutaneously 15 minutes before the 0.5 mg kg-1 subcutaneous dose of morphine. (Emesis normally starts 5 minutes after morphine administration). The ferrets are observed for 2 hours after the morphine dose and the time and numbers of retches and vomits are recorded.

Cisplatin:

The ferrets are weighed and measured for the calculation of body surface area on the day before the experiment. On the day of the experiment each ferret receives an intraperitoneal dose of cisplatin (200 mg m−2). The adenosine $A_1$ receptor agonist is administered subcutaneously immediately after the first emetic episode (approximately 1.5 hours after cisplatin administration). The ferrets are observed for 7 hours after the first emetic episode and the time and numbers of retches and vomits are recorded.

The compounds of Formula I demonstrate the ability to control emesis in this assay.

Determination of Antilipolyitic Properties

Animals. Male Sprague-Dawley rats (380–420 g) were purchased from Simonsen Laboratories (Gilroy, Calif.). All animals received humane care according to the guidelines set forth in The Principles of Laboratory Animal Care formulated by the National Society for Medical Research and the Guide for the Care and Use of Laboratory Animals prepared by the Institute of Laboratory Animal Resources and published by the National Institute of Health (NIH Publication 86-23, revised 1996).

Isolation of Rat Epididymal Adipocytes. Adipocytes were isolated from the epididymal fat pads of rats as described previously (Rodbell, 1964). Briefly, rats were anesthetized using methoxyfluorane and killed by exsanguination. Epididymal fat tissue was removed and placed into a modified Krebs (KRH) solution containing NaCl (100 mM), KCl (4.7 mM), CaCl2 (2.5 mM), NaHCO3 (3.6 mM), MgSO4 (1.19 mM), KH2PO4 (1.18 mM), dextrose (5 mM), pyruvic acid (5 mM), ascorbic acid (1 mM), and HEPES (5 mM), pH 7.4. Visible blood vessels were dissected and excised, and the adipose tissue was minced. Minced tissue was digested with 25 ml of fresh KRH solution containing type I collagenase (1 mg/ml), fatty-acid free BSA [1% (wt/vol)] and nicotinic acid (2_M, to inhibit lipolysis) for 40 to 60 minutes at 37° C. with continuous gentle shaking. The cell suspension was filtered through a nylon-mesh (210_m) to remove undigested tissue fragments. The cell filtrate was washed three times using KRH solution containing 1% fatty acid-free BSA at 37° C. The final adipocyte suspension was either diluted in fresh KRH solution with 1% fatty acid-free BSA for use in cAMP experiments, or used to prepare membranes for radioligand binding assays.

cAMP Assays in Isolated Rat Adipocytes. Aliquots (100 μl, 45,000–90,000 cells) of the freshly prepared adipocyte cell suspension were placed into wells of 24-well cell culture plates containing 0.4 ml of KRH solution containing fatty acid-free BSA (1%), ascorbic acid (1 mM), rolipram (10 μM), cilostamide (1 μM), adenosine deaminase (2 U/ml), and appropriate $A_1$ adenosine receptor agonist(s). An aliquot of 0.5 ml of KRH solution containing 60 nM isoproterenol was added to each well, and incubations proceeded for 4 min in an orbital shaker bath maintained at 37° C. Assays were terminated by the addition of 200 μl of 300 mM HCl to each well to lyse the cells. The concentration of cAMP in the cell lysate was determined using colorimetric direct cAMP kits (Assay Designs, Inc., Ann Arbor, Mich.).

Adipocyte Membrane Preparation and Competition Binding Assays. Freshly isolated adipocytes were added to a chilled solution containing sucrose (0.25 M), EDTA (1 mM), and Tris-HCl (10 mM, pH 7.4) and homogenized with 10 strokes using a motordriven tissue grinder. The homogenate was cooled on ice and the fat layer was discarded. The homogenate was then centrifuged at 500 g for 10 min at 4° C. The supernatant under the fat layer was removed, resuspended in fresh buffer, and homogenized a second time with six strokes using the tissue grinder. Cell membranes were collected by centrifugation of the homogenate at 15,000 g for 15 min. The final membrane pellet was resuspended in a solution containing sucrose (0.25 M), phenylmethylsulfonyl fluoride (0.1 mM), leupeptin (5 μg/ml), aprotinin (5 g/ml), adenosine deaminase (2 U/ml), and Tris-HCl (10 mM) buffer, pH 7.4. The membrane suspension was frozen and stored in liquid nitrogen. For competition binding assays, membrane suspensions were thawed and incubated for 2 hours at room temperature in Tris-HCl (50 mM) buffer containing ADA (1 U/ml), guanosine 5-(imido)triphosphate (100M), and [3H]CPX (1–3nM) and progressively higher concentrations of the competing agent. At the end of incubation, free radioligand was separated from membrane-bound radioligand by filtration through GF/C glass fiber filters (Whatman, Maidstone, UK) using a tissue harvester (Brandel, Inc., Gaithersburg, Md.). Radioactivity was quantified by liquid scintillation counting. Nonspecific binding of [3H]CPX was defined as [3H]CPX bound in the presence of 10 µMN6-cyclopentyltheophylline. Triplicate determinations were performed for each concentration of unlabeled compounds.

Effects of Compounds of Formula I on Heart Rate and Serum NEFA Concentration in Awake Rats.

Heart rate was measured from rats chronically instrumented with telemetry transmitters. For transmitter implantation, a midline laparotomy was performed on anesthetized rats and a transmitter for ECG recording was sutured to the abdominal wall. The two electrocardiographic leads were tunneled through the wall, passed subcutaneously (one to the left shoulder, the other to the right thigh), and secured in place with sutures. Heart rates of awake rats were measured using a Dataquest ART Gold System (Data Sciences International, St. Paul, Minn.). Cardiac electrical activity was recorded for 10-s periods and used to calculate heart rate in beats per minute. After recording of a baseline heart rate, either vehicle (0.9% DMSO in saline, 0.5 ml) or a compound of Formula I was injected into the intraperitoneal cavity of each rat, and heart rate was monitored at intervals for an additional 3 hours.

The effects of a compound of Formula I on heart rate and serum NEFA reduction concentration were determined in separate groups of rats to avoid the effects of animal handling and blood sampling on heart rate. Three days before an experiment, a catheter (0.025-mm outer diameter) was implanted in the left common carotid artery of each rat using aseptic conditions and sterile technique. The catheter was tunneled subcutaneously to the dorsal surface. After recovery from anesthesia, rats were placed in metabolic cages to facilitate handling and blood sampling. Blood samples (0.2 ml) were drawn before and at various time points after i.p. injection of either a compound of Formula I or vehicle (DMSO in saline). A 0.4-ml volume of 1% sodium citrate in saline was administered after withdrawal of each blood sample to replace blood volume and prevent clotting in the carotid artery catheter. Serum was collected from each sample after centrifugation of the clotted blood. Serum samples were stored at _80° C. until analysis. Serum NEFA concentration was determined using an enzymatic colorimetric assay kit (Wako Chemicals, Richmond, Va.).

The antipolytic properties of compounds of Formula I in rats with catecholamines-stimulated NEFA levels were studied in rats with indwelling catheters (described above). Norepinephrine was delivered either by i.v. infusion into the jugular vein at 3 µg/kg/min for 30 minutes or by i.p. injection (60 µg/kg). A compound of Formula I was delivered by i.p. injection either before or after norepinephrine to determine whether the increase in NEFA concentrations caused by norepinephrine could be prevented or reversed by the compound of Formula I.

The compounds of Formula I demonstrated antipolytic properties in this assay. For example, oral administration of (4S,2R,3R,5R)-2-[6-(cyclopentylamino)purin-9-yl]-5-{2-[2-fluorophenyl]-ethynyl}oxolane-3,4-diol at a dose level of 1 mg/Kg provided an initial 40% reduction of non-esterified free fatty acid (NEFA) that was maintained for 1 hour, after which time the plasma levels of NEFA returned to normal in 2 hours. Oral administration of (4S,2R,3R,5R)-2-[6-(cyclopentylamino)purin-9-yl]-5-{2-[2-fluorophenyl]-ethynyl}oxolane-3,4-diol at a dose level of 2.5 mg/Kg provided an initial 60% reduction of non-esterified free fatty acid (NEFA) that was maintained for 90 minutes, after which time the plasma levels of NEFA returned to normal in 4 hours.

At dose levels of 1 mg/kg, 2.5 mg/kg, and 5 mg/kg, no effect on heart rate was observed.

What is claimed is:

1. A compound of the formula:

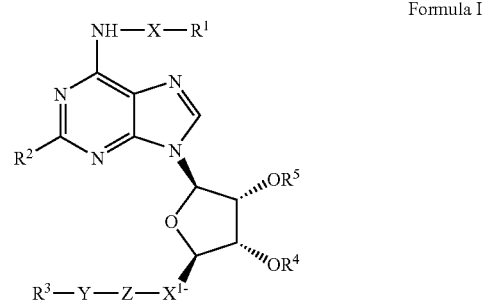

Formula I wherein:
  $R^1$ is optionally substituted cycloalkyl, optionally substituted heterocyclyl, optionally substituted aryl, or optionally substituted heteroaryl;
  $R^2$ is hydrogen, halo, trifluoromethyl, or cyano;
  $R^3$ is optionally substituted cycloalkyl, optionally substituted aryl, optionally substituted heteroaryl, or optionally substituted heterocyclyl,
  $R^4$ and $R^5$ are independently hydrogen or optionally substituted acyl;
  X is a covalent bond or lower alkylene optionally substituted by cycloalkyl;
  $X^1$ is a covalent bond or alkylene;
  Y is a covalent bond or lower alkylene optionally substituted by hydroxy or cycloalkyl; and
  Z is —C≡C—, —$R^6$C=C$R^7$—, or —CH$R^6$CH$R^7$—, in which $R^6$ and $R^7$ at each occurrence are hydrogen or lower alkyl.

2. The compound of claim 1, wherein Z is —C≡C—.

3. The compound of claim 2, wherein X, $X^1$ and Y are covalent bonds.

4. The compound of claim 3, wherein $R^1$ is optionally substituted cycloalkyl, optionally substituted heterocyclyl, or optionally substituted heteroaryl.

5. The compound of claim 4, wherein $R^2$, $R^4$ and $R^5$ are hydrogen.

6. The compound of claim 5, wherein $R^3$ is optionally substituted aryl.

7. The compound of claim 6, wherein $R^1$ is optionally substituted cyclopentyl or optionally substituted tetrahydrofuranyl and $R^3$ is optionally substituted phenyl.

8. The compound of claim 7, wherein $R^1$ is cyclopentyl and $R^3$ is 2-fluorophenyl, namely (4S,2R,3R,5R)-2-[6-(cyclopentylamino)purin-9-yl]-5-[2-(2-fluourophenyl)ethynyl]oxolane-3,4-diol.

9. The compound of claim 7, wherein $R^1$ is cyclopentyl and $R^3$ is 2-trifluoromethylphenyl, namely (4S,2R,3R,5R)-

2-[6-(cyclopentylamino)purin-9-yl]-5-{2-[2-(trifluoromethyl)-phenyl]ethynyl}oxolane-3,4-diol.

10. The compound of claim 7, wherein $R^1$ is tetrahydrofuran-3-yl and $R^3$ is 2-fluorophenyl, namely (4S,2R,3R,5R)-2-[6-(oxalan-3-ylamino)purin-9-yl)]-5-{2-[2-fluorophenyl]ethynyl}-oxolane-3,4diol.

11. The compound of claim 7, wherein $R^1$ is tetrahydrofuran-3-yl and $R^3$ is 2-trifluoromethylphenyl, namely (4S,2R,3R,5R)-2-[6-(oxalan-3-ylamino)purin-9-yl]-5-{2-[2-(trifluoromethyl)phenyl]-ethynyl}oxolane-3,4-diol.

12. The compound of claim 5, wherein $R^3$ is optionally substituted heteroaryl.

13. The compound of claim 12, wherein $R^1$ is optionally substituted cyclopentyl or optionally substituted tetrahydrofuranyl and $R^3$ is optionally substituted thienyl.

14. The compound of claim 13, wherein $R^1$ is cyclopentyl or tetrahydrofuran-3-yl and $R^3$ is thien-2-yl.

15. The compound of claim 1, wherein Z is —$R^6C$=$CR^7$—, in which $R^6$ and $R^7$ are both hydrogen.

16. The compound of claim 15, wherein X, $X^1$ and Y are covalent bonds.

17. The compound of claim 16, wherein $R^1$ is optionally substituted cycloalkyl.

18. The compound of claim 17, wherein $R^2 R^4$ and $R^5$ are hydrogen.

19. The compound of claim 18, wherein $R^3$ is optionally substituted aryl or optionally substituted heteroaryl.

20. The compound of claim 19, wherein $R^1$ is cyclopentyl and $R^3$ is 5-chlorothien-2-yl, 4-methylisoxazol-3-yl or 3,5-dimethylisoxazol-4-yl.

21. The compound of claim 19, wherein $R^1$ is cyclopentyl and $R^3$ is 2-methyphenyl, namely 5-[2-(2-methylphenyl)vinyl](4S,2R,3R,5R)-2-[6-(cyclopentylamino)purin-9-yl]oxolane-3,4-diol.

22. The compound of claim 19, wherein $R^1$ is cyclopentyl and $R^3$ is phenyl, namely 5-[2-(phenyl)vinyl](4S,2R,3R,5R)-2-[6-(cyclopentylamino)purin-9-yl]oxolane-3,4-diol.

23. A pharmaceutical composition comprising at least one pharmaceutically acceptable excipient and a therapeutically effective amount of a compound of claim 1.

* * * * *